United States Patent
Henry et al.

(10) Patent No.: US 8,371,293 B2
(45) Date of Patent: Feb. 12, 2013

(54) BLADDER CUSHION, FOREHEAD CUSHION, HEADGEAR STRAPS, HEADGEAR CAP AND/OR CHINSTRAP

(75) Inventors: Robert Edward Henry, Roseville (AU); Philip Rodney Kwok, Chatswood (AU); Karthikeyan Selvarajan, Thornleigh (AU); Philip John Gunning, North Rocks (AU); Christopher John Baxter, Chatswood (AU)

(73) Assignee: ResMed Limited, Bella Vista (AU)

( * ) Notice: Subject to any disclaimer, the term of this patent is extended or adjusted under 35 U.S.C. 154(b) by 1017 days.

(21) Appl. No.: 12/086,288

(22) PCT Filed: Dec. 12, 2006

(86) PCT No.: PCT/AU2006/001886
§ 371 (c)(1),
(2), (4) Date: Dec. 1, 2008

(87) PCT Pub. No.: WO2007/068044
PCT Pub. Date: Jun. 21, 2007

(65) Prior Publication Data
US 2010/0024811 A1     Feb. 4, 2010

Related U.S. Application Data

(60) Provisional application No. 60/750,802, filed on Dec. 16, 2005, provisional application No. 60/833,784, filed on Jul. 28, 2006.

(51) Int. Cl.
*A62B 18/02* (2006.01)

(52) U.S. Cl. ......... 128/200.24; 128/200.26; 128/206.25; 623/7

(58) Field of Classification Search .................. 482/35, 482/27, 26, 23; 128/202.23, 206.25, 652.1, 128/655.3; 5/637, 638, 446
See application file for complete search history.

(56) References Cited

U.S. PATENT DOCUMENTS

| 4,811,730 | A | | 3/1989 | Milano |
| 4,971,051 | A | | 11/1990 | Toffolon |
| 5,037,436 | A | * | 8/1991 | Heaston ........................ 623/7 |
| 5,243,971 | A | | 9/1993 | Sullivan |
| 5,813,946 | A | * | 9/1998 | Lin et al. .................... 482/27 |
| 6,397,847 | B1 | | 6/2002 | Scarberry et al. |
| 6,834,650 | B1 | | 12/2004 | Fini et al. |
| 2002/0029780 | A1 | | 3/2002 | Frater |

(Continued)

FOREIGN PATENT DOCUMENTS

| DE | 198 07 818 | 9/1999 |
| EP | 541569 | 3/1996 |
| WO | WO 2004/078231 | 9/2004 |
| WO | WO 2005/009521 | 2/2005 |
| WO | WO 2006/050559 | 5/2006 |

OTHER PUBLICATIONS

German Office Action dated Apr. 8, 2008 issued in corresponding German Application No. 10 2006 000 534.145 with English translation.

(Continued)

*Primary Examiner* — Jerome W Donnelly
(74) *Attorney, Agent, or Firm* — Nixon & Vanderhye P.C.

(57) ABSTRACT

A cushion for a patient interface includes two or more bladders arranged in concentric relation. Each of the bladders includes a face-contacting portion adapted to engage the patient's face, and each of the bladders is adapted to be pressurized independently from one another. At least one of the bladders is an active bladder that is pressurized to at least a sealing pressure to form a continuous seal with the patient's face in use.

40 Claims, 30 Drawing Sheets

U.S. PATENT DOCUMENTS

| | | |
|---|---|---|
| 2003/0221691 A1 | 12/2003 | Biener |
| 2004/0107968 A1 | 6/2004 | Griffiths |
| 2004/0118406 A1 | 6/2004 | Lithgow et al. |
| 2004/0244800 A1 | 12/2004 | Gradon |
| 2005/0241644 A1 | 11/2005 | Gunaratnam et al. |
| 2006/0118117 A1 | 6/2006 | Berthon-Jones |
| 2006/0185675 A1 | 8/2006 | Colin |

OTHER PUBLICATIONS

Brook R.J. [editor]: Processing of Ceramics. In: Cahn R.W. [editor]: Materials Science and Technology, vol. 17, Part A, VCH Verlagsgesellschaft, Weinheim, 1996, ISBN 3-527-26830-8.

\* cited by examiner

BLADDER CUSHION, FOREHEAD CUSHION, HEADGEAR STRAPS, HEADGEAR CAP AND/OR CHINSTRAP

CROSS REFERENCE TO PRIORITY APPLICATIONS

This application is the U.S. national phase of International Application No. PCT/AU2006/001886, filed Dec. 12, 2006 which designated the U.S. and claims the benefit of U.S. Provisional Application Nos. 60/833,784, filed Jul. 28, 2006, and 60/750,802, filed Dec. 16, 2005, each of which is incorporated herein by reference in its entirety.

FIELD OF THE INVENTION

The present invention relates to a patient interface used for treatment, e.g., of sleep disordered breathing (SDB) such as obstructive sleep apnea (OSA).

BACKGROUND OF THE INVENTION

Patients who suffer from obstructive sleep apnea can use continuous positive airway pressure (CPAP) therapy to maintain the upper airway open while they are asleep. CPAP therapy is applied to the patient using a mask, tubing, and a flow generator. All of these components encompass the air delivery system provided to the patient.

One problem for patients who undergo CPAP therapy is irritation and skin ailments, e.g., sores, caused by wearing a mask. The problem is a result of the mask cushion compressing or applying pressure to the patient's skin in a similar region for a prolonged length of time. Blood capillaries may be squashed or impinged upon which may cause a blockage or partial blockage to circulation. This may result in inflammation and/or redness of the skin and/or facial numbness. These problems may cause a patient to cease therapy.

A known solution includes buying two or more different masks and wearing them alternately. Another known solution includes switching between two different styles of mask, e.g., switch between a full-face mask and a nasal mask or switch between a nasal cushion and nasal pillows. Yet another known solution includes repositioning the mask on the patient's face if the patient wakes up during the night. These solutions have several drawbacks, e.g., requires the purchase of multiple masks and/or prevents patient from a full night of sleep.

Another problem is sweat or humidification caused by wearing a mask. The sweat or humidification can block the patient's skin ducts, which may cause irritation. Moisture held against the skin can also soften the skin rendering it more susceptible to damage. Therefore, it is desirable to allow moisture removal from the skin surface.

Another problem patients have with masks is that they are uncomfortable, and it can be difficult for patients to relax when wearing one. If a patient cannot relax enough to fall asleep, then the mask is ineffective as treatment for sleeping disorders as it is preventing the patient from having a full nights sleep.

Another problem with masks is mask leak. Leaks between the cushion and the patient's skin can be generated after the patient has fallen asleep due to the patient's movements. These leaks may cause the mask to stop delivering treatment by reducing the mask pressure and/or by waking the patient. Either of these occurrences will result in the patient not receiving a good nights sleep.

Leaks tend to occur at specific regions of the cushion seal. It is known that additional pressure to stop the leaks may be applied by tightening headgear straps. However, this approach tends to tighten the entire cushion against the patient's face, which can lead to discomfort or sores.

Thus, there is a need for an improved patient interface that does not suffer from the above-mentioned drawbacks.

SUMMARY OF THE INVENTION

One aspect of the invention relates to a structure changing portion within a mask to modify body contacting regions during or between treatment sessions to allow tissue to repair and relax, to improve fit and comfort, and to minimize contact pressure sores.

Another aspect of the invention relates to alternating the contact areas of a cushion to reduce irritation, and hence reduce the amount of time that pressure is applied to one region of the patient's skin.

Another aspect of the invention relates to dynamically controlling the contact pressure of a cushion.

Another aspect of the invention relates to alternating the magnitude and/or location of cushion contact pressure to provide a cushion with a massaging effect. The massaging effect relaxes the patient and prevents irritation, thereby aiding the patient in falling asleep.

Another aspect of the invention relates to alternating contact pressure points of a cushion to cause small movement of the cushion which can seal leaks.

Another aspect of the invention relates to a patient interface structured to increase force at the specific region where leaks occur.

Another aspect of the invention relates to a patient interface in the form of a massage mask including a cushion structured to change skin to cushion contact areas and/or change skin to cushion contact forces. These changes may occur at discreet regions of the cushion and may be selectable.

Another aspect of the invention relates to a patient interface, e.g., mask, that improves patient comfort by being able to change form, temperature, move or remove moisture during a treatment session and/or between treatment sessions.

Another aspect of the invention relates to a cushion for a patient interface. The cushion includes two or more bladders arranged in concentric relation. Each of the bladders includes a face-contacting portion adapted to engage the patient's face, and each of the bladders is adapted to be pressurized independently from one another. At least one of the bladders is an active bladder that is pressurized to at least a sealing pressure to form a continuous seal with the patient's face in use.

Another aspect of the invention relates to a cushion for a patient interface. The cushion includes a bladder including a face-contacting portion adapted to engage the patient's face. The bladder includes one or more partition walls that divide the bladder into two or more cells, and each of the cells is adapted to be pressurized independently from one another. Each of the cells is pressurized to at least a sealing pressure to form a portion of a continuous seal with the patient's face in use.

Another aspect of the invention relates to a cushion for a patient interface. The cushion includes two or more bladders arranged in concentric relation. Each of the bladders includes a face-contacting portion adapted to engage the patient's face. Each of the bladders includes one or more partition walls that divide each bladder into two or more cells, and each of the cells of each bladder is adapted to be pressurized independently from one another. Selected cells of selected bladders are pressurized to at least a sealing pressure so that the selected cells cooperate to form a continuous seal with the patient's face in use.

Another aspect of the invention relates to a cushion for a patient interface; The cushion includes a bladder including a face-contacting portion adapted to engage the patient's face. The bladder is adapted to be pressurized so that pressure within the bladder is alternated at a predetermined frequency to alternate contact pressure provided by the bladder. Pressure within the bladder is at least a sealing pressure to form a continuous seal with the patient's face in use.

Another aspect of the invention relates to a forehead cushion for a patient interface. The forehead cushion includes a bladder including a forehead-contacting portion adapted to engage the patient's forehead. The bladder is adapted to be pressurized.

Another aspect of the invention relates to a method for sealing a patient's face during a treatment session including delivery of breathable gas. The method includes engaging a cushion with the patient's face to form a continuous seal, and moving the contact position provided by the cushion at least once during the treatment session while maintaining the continuous seal.

Another aspect of the invention relates to a mask for sealing a patient's face during a treatment session including delivery of breathable gas. The mask includes a face contacting portion adapted to contact the patient's face. The face contacting portion is structured such that at least one change to a contact pressure point, a contact pressure region, and/or a shape of the face contacting portion may be made during or between treatment sessions to improve comfort and/or maintain skin capillary blood flow.

Another aspect of the invention relates to a mask for sealing a patient's face during a treatment session including delivery of breathable gas. The mask includes a face contacting portion adapted to contact the patient's face. The face contacting portion is adapted to oscillate to improve comfort and/or maintain skin capillary blood flow.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

1. Modes of Operation

Figure 1:
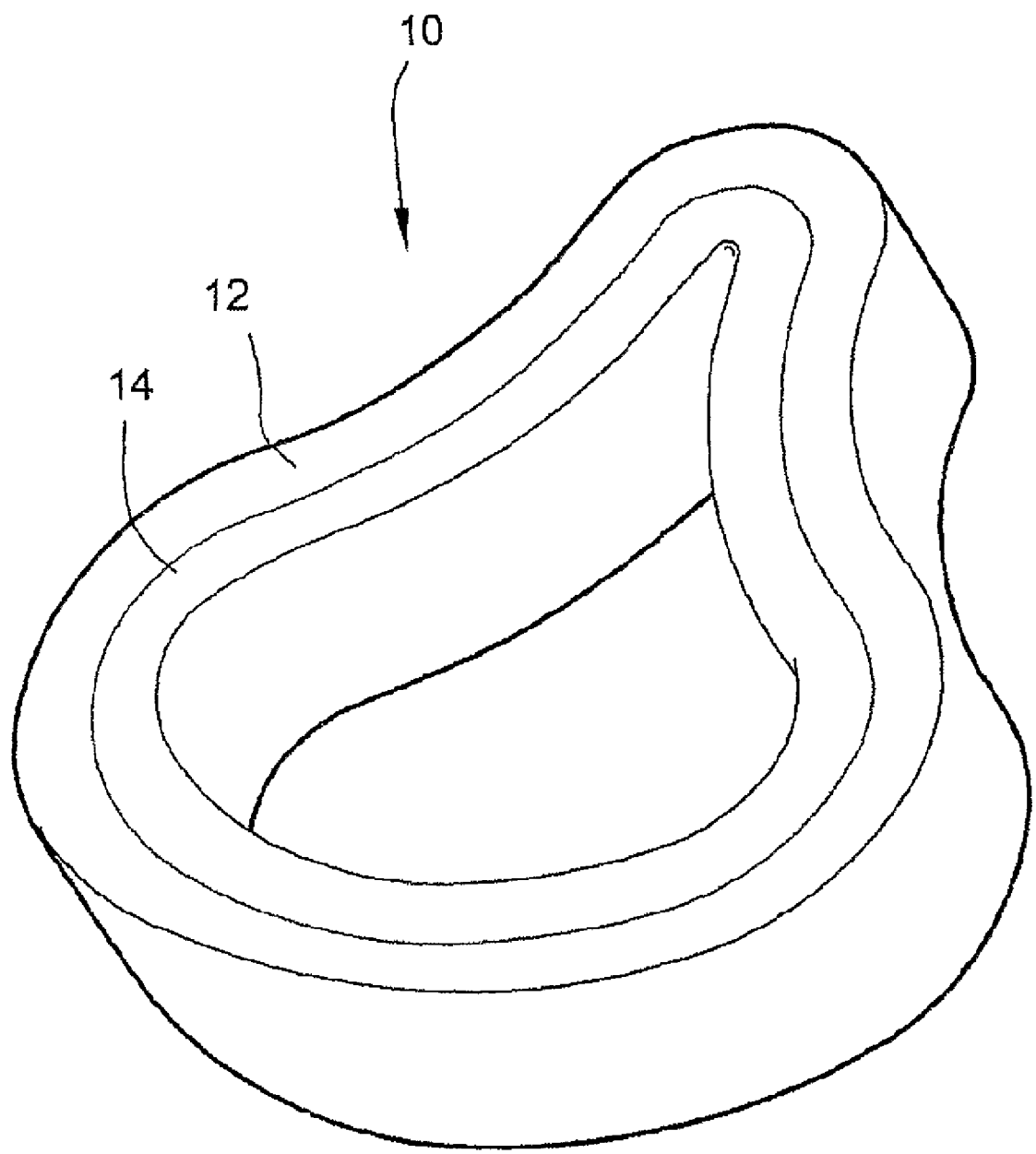
FIG. 1 is a perspective view of a bladder cushion for a patient interface according to an embodiment of the present invention.

One aspect of the invention relates to a patient interface, e.g., mask, that is operable in different modes of operation, e.g., an alternating mode and a massage mode. In alternating mode, the patient interface operates by alternating the contact pressure and/or contact positions of the cushion to the patient. Massage mode is similar to alternating mode but alternates the contact pressure and/or contact positions at a higher frequency and at more abrupt transitions than alternating mode.

1.1 Single Night Alternating Mode

An aspect of alternating mode is to reduce or eliminate sores and irritations that result from wearing a mask all night. Thus, alternating mode may be a single night alternating mode that runs for the majority of the night or sleep period after the patient has fallen asleep. In an embodiment, this mode may be programmed to only activate after a set amount of time. For example, this time may be the same as the ramp time of the flow generator.

Single night alternating mode operates by alternating the contact pressure and/or contact positions of the cushion to the patient over a single night. The frequency of alternation will be relatively low, e.g., minutes rather than seconds, and may be settable. The transition between contact pressure and/or between contact positions will be gradual. The frequency and transition rate may be determined by patient comfort. If the frequency is too large and/or if the transition is too abrupt, it can arouse the patient. In one embodiment, the contact pressure and/or contact positions of the cushion may alternate every 20 minutes. In another embodiment, the contact pressure and/or contact positions of the cushion may alternate every hour. However, any interval length is possible depending on application.

1.2 Night to Night Alternating Mode

In another embodiment, alternating mode may be a night to night alternating mode. This mode is essentially the same as the single night alternating mode except that the frequency of alternations is one night. This means that each night the patient wears the mask the contact pressures and/or contact positions will be different. That is, the mask will feel like a different mask each night. In other embodiments, the alternating mode alternates over any other suitable time period (e.g., every two days, a week, etc.).

1.3 Massage Mode

Massage mode is intended to relax the patient and/or soothe the skin or facial tissue and hence assist the patient in falling asleep sooner. Massage mode will generally only be run at the start of treatment (e.g., during the ramp time of the flow generator), but could be run periodically throughout the night to promote blood circulation. The length of time massage mode runs may be settable, and in general may be set the same as the ramp time of the flow generator.

Massage mode works by alternating the contact pressure and/or contact positions at a higher frequency than alternating mode. Also, the transitions will be more abrupt than alternating mode. These variables may be settable to simplify use, and massage cycles may be programmed into a mask controller. For example, a "firm" massage may include high contact pressures, low frequency, and long transition times. A "rapid" massage may include low contact pressures, high frequency, and more abrupt transition times. This rapid massage mode could be used to awaken a patient at the end of the treatment session.

1.4 Leak Control

Leak control is intended to restabilize the interface between the cushion and the patient to reduce or eliminate leak. When a leak is detected by the flow generator, the contact pressures and contact positions may be modified, e.g., by moving the contact position and/or by increasing the contact pressure.

1.5 Determining Optimal Sealing Force

The modifiable contact pressure allows the mask to automatically determine the ideal sealing force. The flow generator will monitor mask leak as the flow generator ramps up to therapy pressure, and the contact pressure may be modified to eliminate any leak. When the therapy pressure is reached, the sealing force can be reduced until leak is detected. The sealing force can then be increased again to eliminate the leak. The contact pressure modification can be repeated at intervals throughout the night to ensure that excessive sealing forces are not being used. In an embodiment, this process may occur every 30 minutes, but could be done at any suitable interval.

Regions around the face may be identified as where leaks typically occur, e.g., nasal bridge, cheek and chin regions. These regions may be selected to optimize comfort, and may be manually selected by the patient. For example, if there is leak around the patient's nose when the patient initially fits the mask, the patient may simply select the nasal region for a pressure increase.

2. Bladder Cushions

One way to control the magnitude and location of the pressure in the cushion is to use fluid-filled bladders for cushions. The following includes descriptions of bladder cushions according to several illustrated embodiments of the present invention.

In each of the illustrated embodiments, the bladder cushion may be pressurized with a fluid, which includes gases, e.g., air, and liquids. It may also be possible to use a solid to control bladder pressure by means of a relatively soft material, e.g., a low durometer elastomer, with approximate shore hardness of 0-30.

In each of the illustrated embodiments, the cushions are full-face cushions that provide a seal around the patient's nose and mouth to enable the delivery of breathable gas to the patient's nose and mouth. However, aspects of the present invention may be applicable to other breathing arrangements, e.g., a nasal cushions, a mouth cushions, nasal prongs, total face, etc. In an embodiment, the bladder cushions may include an additional membrane over the top of the bladders to assist in seal.

Also, in an embodiment, a fluid-filled bladder may only be provided in one or more portions of a cushion, e.g., fluid-filled bladder only provided in a nasal bridge region of the cushion.

Bladder cushions may also reduce deadspace. This arrangement may be desirable when the mask is to be used with very low treatment pressures or when $CO_2$ rebreathing is a concern.

Each bladder cushion is adapted to be removably or permanently connected to a frame of a patient interface. Each bladder cushion includes a non-face-contacting portion structured to be connected to the frame, and a face-contacting portion structured to engage the patient's face and provide a seal.

In the illustrated embodiments, the face-contacting portion of each bladder cushion has a generally triangular shape and is structured to contact the nasal bridge, cheek, and chin region of the patient. However, the face-contacting portion may have other suitable shapes, e.g., a generally trapezoidal shape. As illustrated, each bladder cushion includes a pair of cheek regions to provide a seal along the cheeks and the sides of the mouth, a chin region to provide a seal below the chin of the patient, and a nasal bridge region to provide a seal along the patient's nasal bridge.

2.1 Concentric Bladder Cushions

FIG. 1 illustrates a cushion 10 including two concentric bladders 12, 14, e.g., air bladders. However, more than two bladders may be used. In use, each bladder 12 and 14 may be pressurized independently to provide a seal with the patient's face. The cushion 10 may operate in alternating or massage mode to alternate the contact pressure and/or contact position of the cushion 10.

2.1.1 Alternating Mode

At any given time, one bladder will be pressurized to the sealing pressure (i.e., the amount of pressure required to seal the cushion to the patient's face), and the other bladder or bladders will be deflated (e.g., to atmospheric pressure). The active or pressurized bladder will alternate throughout the night. For example, the bladders 12 and 14 of cushion 10 may alternate as the active bladder through the night.

At no time will all the bladders be deflated when changing the active bladder. To achieve this, the transition process includes inflating the non-active or deflated bladder to the sealing pressure, and deflating the currently active bladder only when the sealing pressure of the other bladder is achieved. Transitioning in this manner will prevent leaks caused by no bladder being inflated to sealing pressure.

In an embodiment, one bladder may be pressurized to the sealing pressure, and the other bladder or bladders may be deflated to a pressure below atmospheric pressure (creating suction up the pressure source line). The resulting negative pressure will result in lifting all or some of the other bladders off the patient's face. For example, in the concentric bladder cushion, the bladder or bladders that are not active could have their pressure reduced to below atmospheric resulting in the active bladder being the only bladder in contact with the patient's skin.

2.1.2 Massage Mode

As with alternating mode, at least one bladder is pressurized to the sealing pressure at any given time. The massaging effect is achieved by both alternating the magnitude and location of the pressure. For example, one bladder is inflated to sealing pressure, and another bladder will inflate to sealing pressure or at a higher set pressure for a firmer massage. Only when the other bladder has reached sealing pressure will the previously inflated bladder be allowed to deflate. This process of inflating and deflating the two bladders will occur at a high frequency to massage the patient's face.

2.2 Partitioned Single Bladder Cushion

Figure 2:
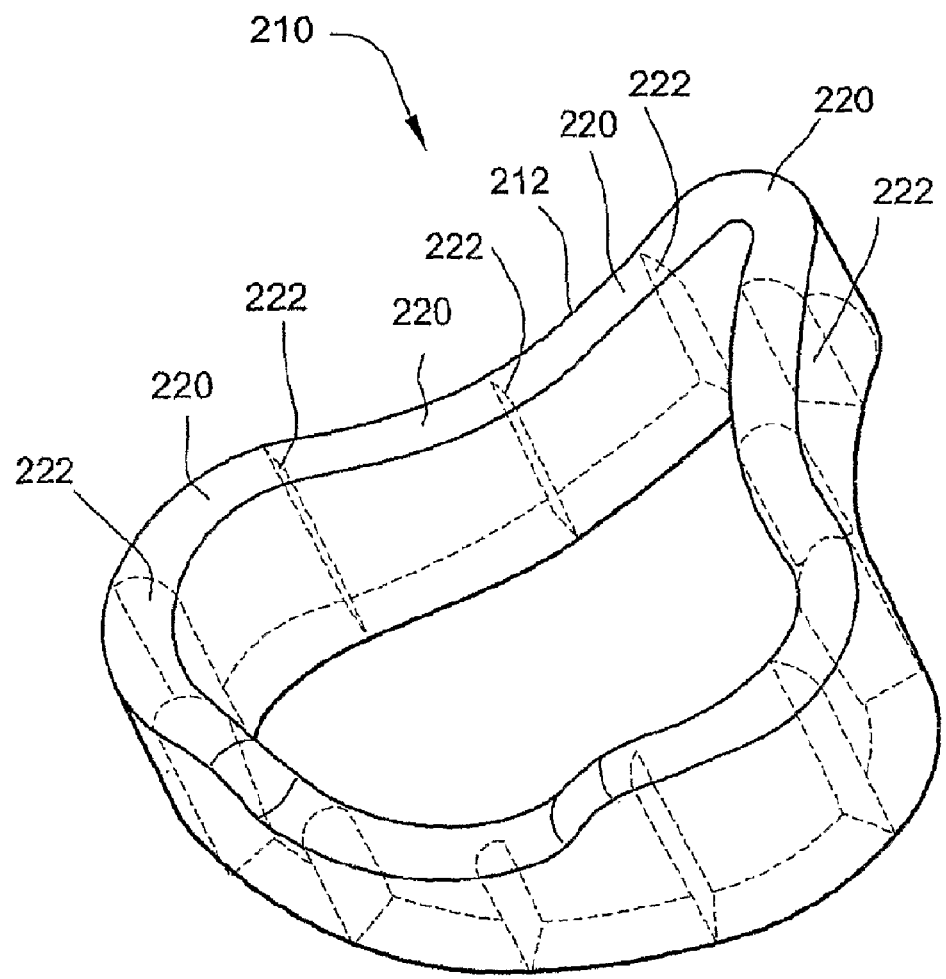
FIG. 2 is a perspective view of a bladder cushion for a patient interface according to another embodiment of the present invention.

FIG. 2 illustrates a cushion 210 including a single inflatable bladder 212 that is partitioned into a plurality of cells 220. As illustrated, partition walls 222 are provided within the bladder 212 to define the cells 220. The partition walls 222 extend normal to the cushion perimeter. In use, each cell 220 may be pressurized independently to provide a seal with the patient's face. The cushion may operate in alternating or massage mode to alternate the contact pressure of the cushion 210.

The advantage of having cells (versus no cells) is that the sealing pressure around the cushion can be tuned more accurately to provide greater patient comfort. In an embodiment, pairs or patterns of cells may be pressurized in unison to minimize complexity. In another embodiment, regions may be identified, e.g., nasal bridge, cheek, and chin regions, and these regions may be pressurized independently. For example, the cushion may act symmetrically wherein corresponding cells on each side of the cushion may be pressurized together. This arrangement would halve the number of valves required to control cushion inflation. This partitioned cushion allows greater control of sealing pressure throughout the mask, however pressure contact positions will remain constant.

2.2.1 Alternating Mode

All cells will initially be inflated to sealing pressure. A higher pressure will be set in the cushion controller, and this higher pressure will be determined by patient comfort (the pressure shall not be so great as to arouse the patient at any stage of the night). During the night, the pressure of the cells will oscillate throughout the range of pressures, from minimum to maximum pressures. The cells may inflate in unison or may inflate independently of each other.

2.2.2 Massage Mode

Massage mode will perform the same way as alternating mode, except at a higher frequency. All cells will initially be inflated to sealing pressure, and the cells' pressure will be oscillated to a higher pressure. This higher pressure will not necessarily be the same as the set pressure in alternating mode as it serves a different purpose (i.e., massage vs. irritation prevention).

2.3 Partitioned Multiple Bladder Cushion

Figure 3:
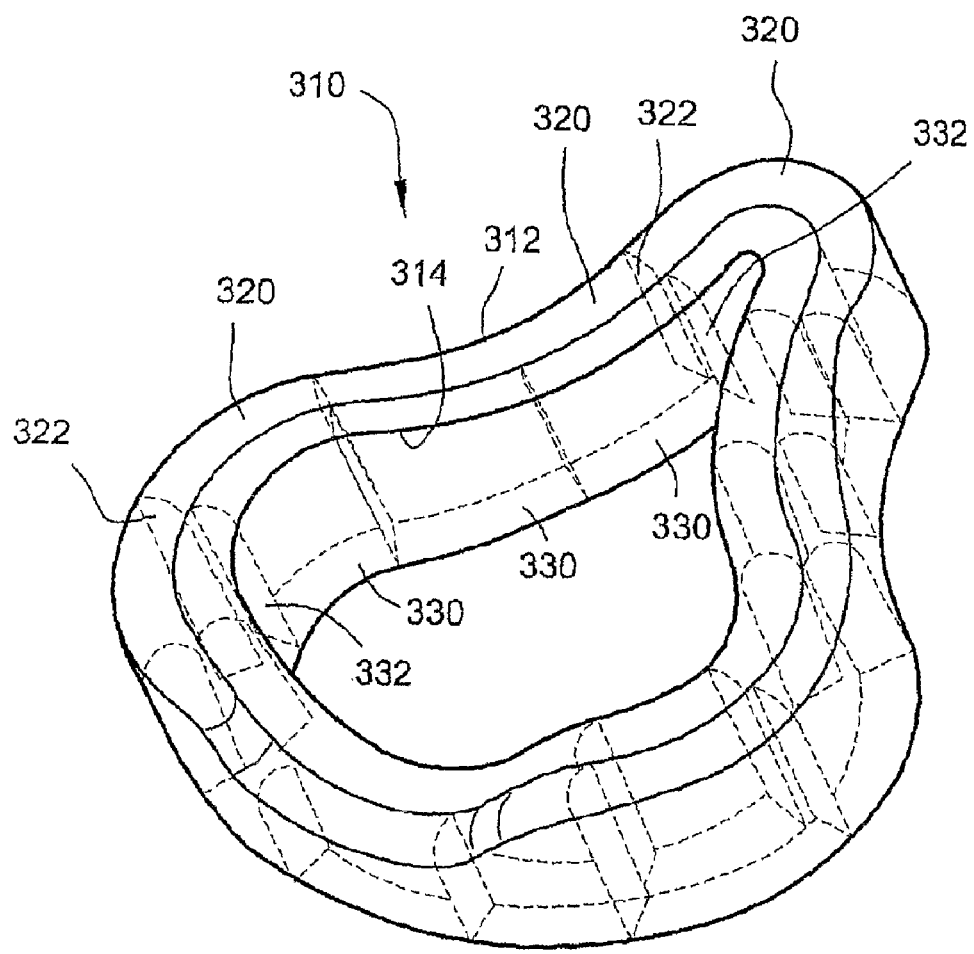
FIG. 3 is a perspective view of a bladder cushion for a patient interface according to another embodiment of the present invention.

FIG. 3 illustrates a cushion 310 including two concentric bladders 312, 314 with each bladder 312, 314 partitioned into a plurality of cells 320, 330, respectively. However, more than two partitioned bladders may be used. As illustrated, partition walls 322, 332 (extending normal to the cushion perimeter) are provided within respective bladders 312, 314 to define the cells 320, 330 within respective bladders 312, 314. In use, each cell 320, 330 may be pressurized independently to provide a seal with the patient's face. The cushion 310 may operate in alternating or massage mode to alternate the contact pressure and/or contact position of the cushion 310.

Figure 4:
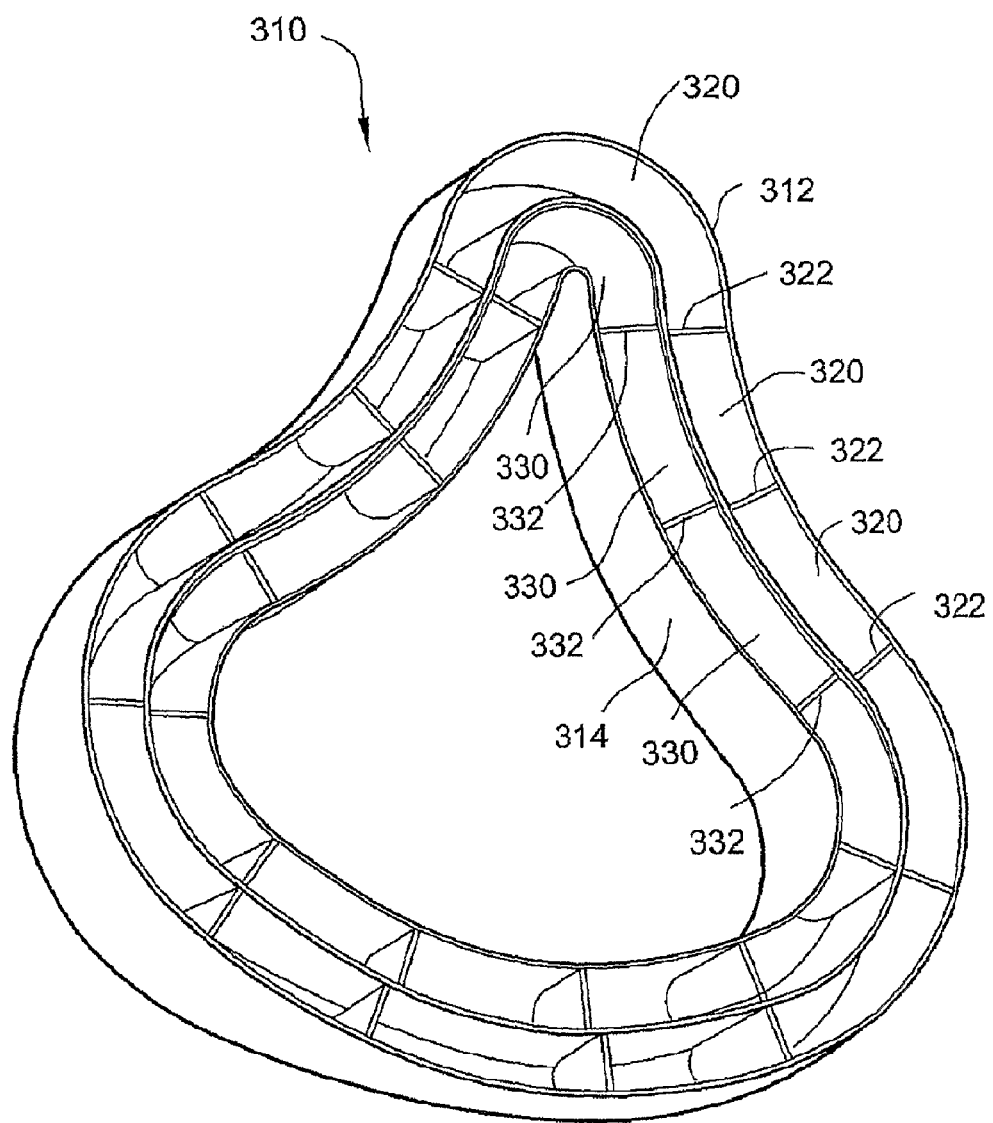
FIGS. 4-5 illustrate alternative cell arrangements for the bladder cushion shown in FIG. 3.
Figure 5:
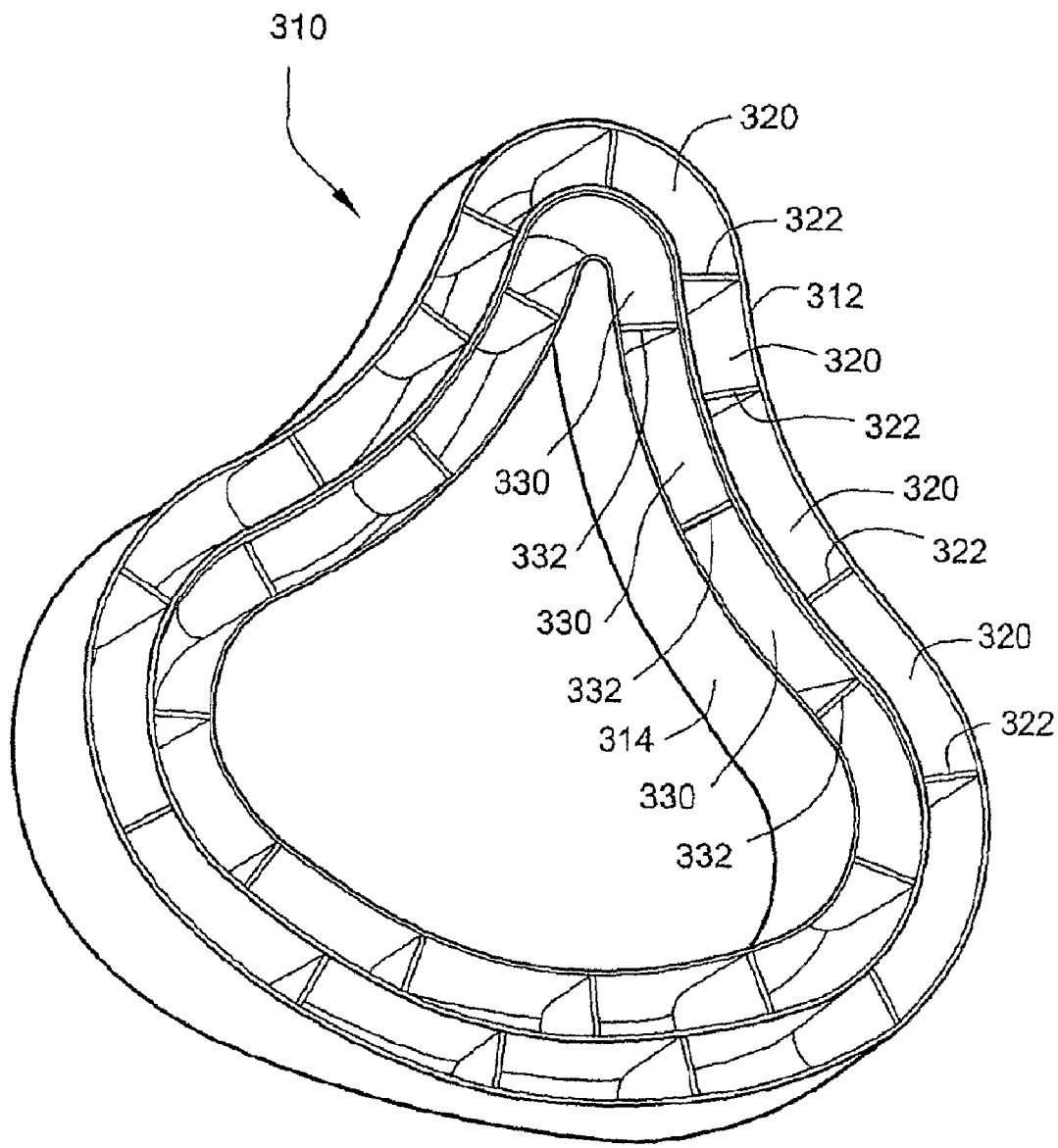
Figure 6:
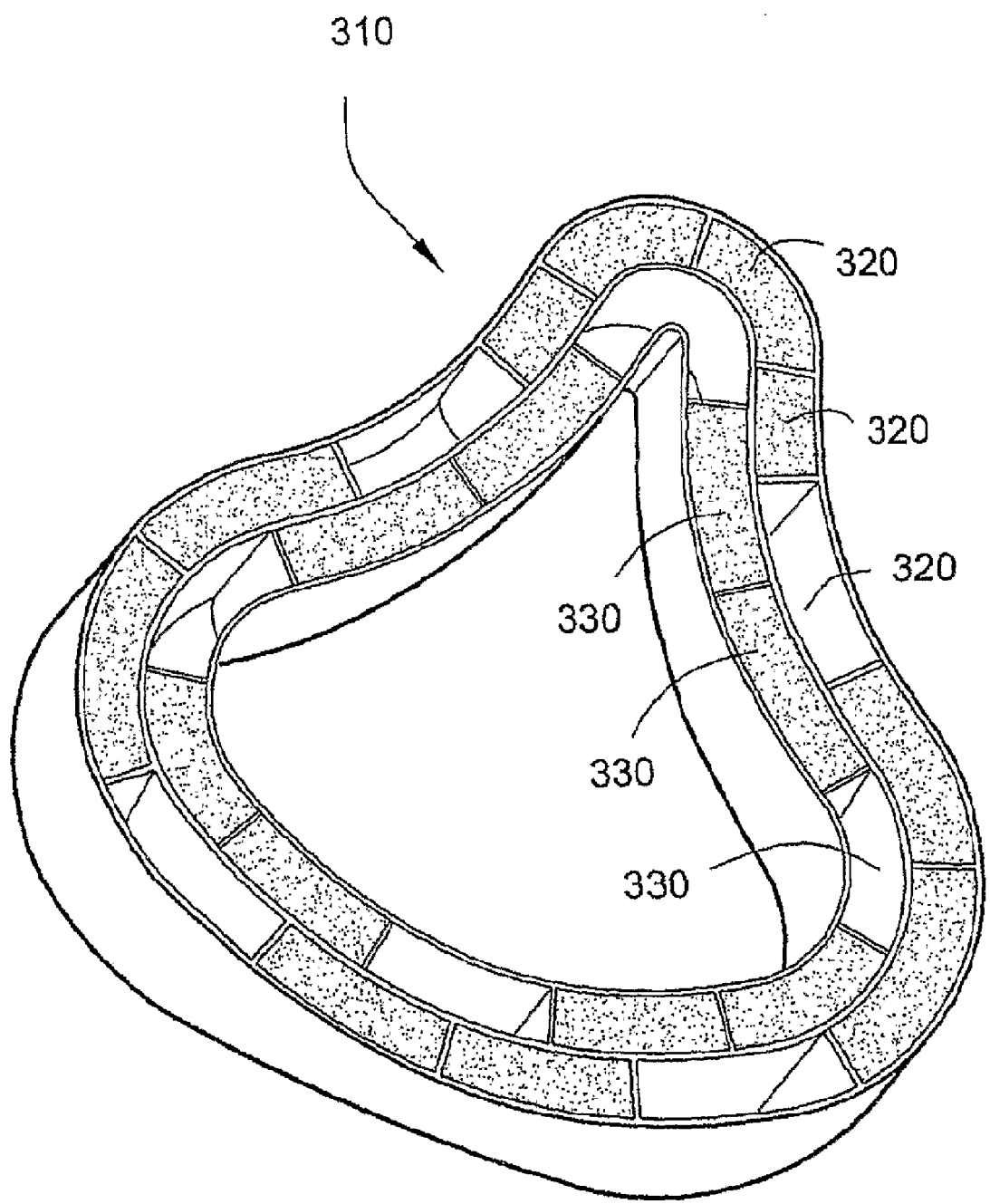
FIGS. 6-10 illustrate alternative inflation patterns for the cell arrangement shown in FIG. 5.
Figure 7:
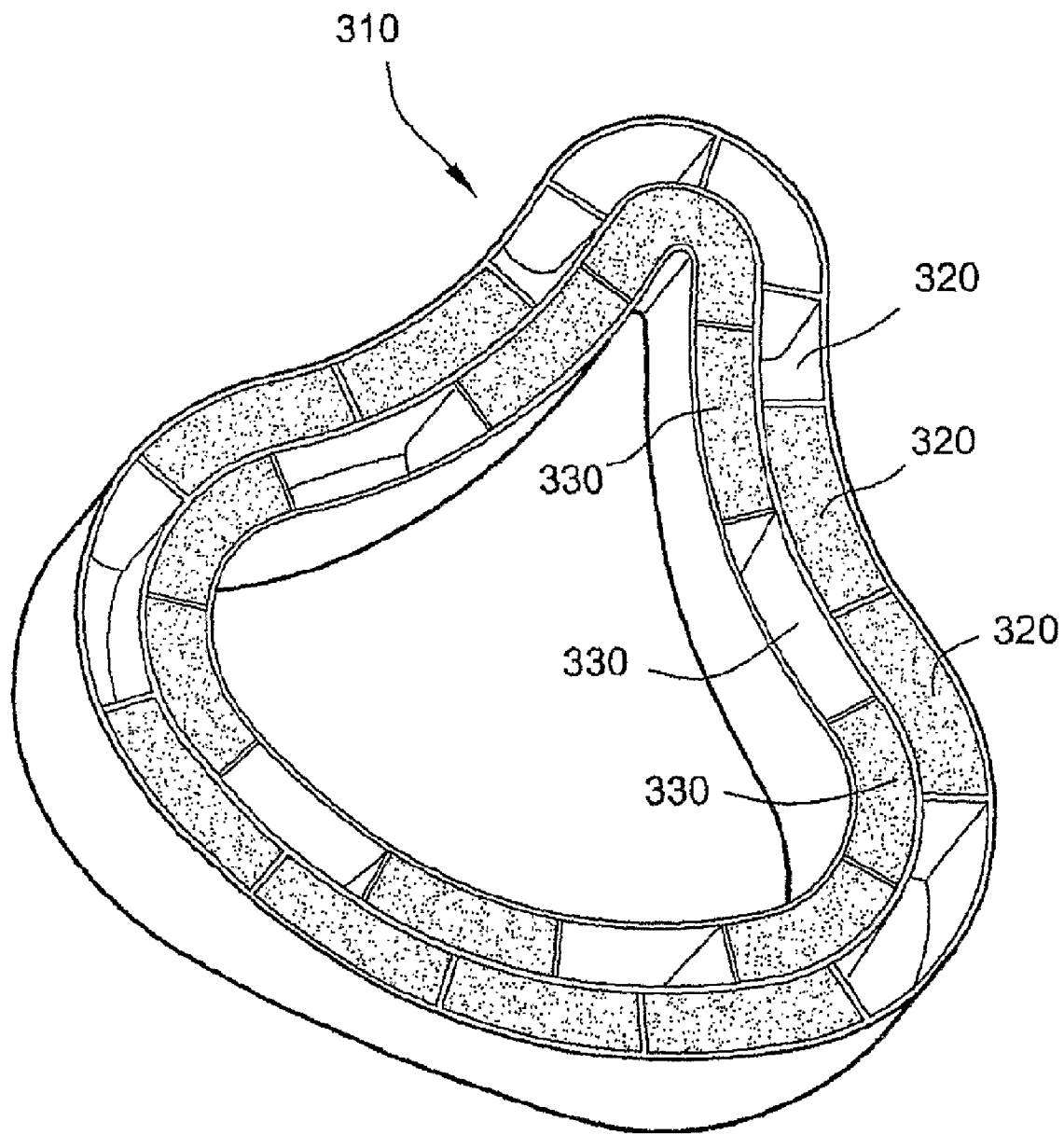
Figure 8:
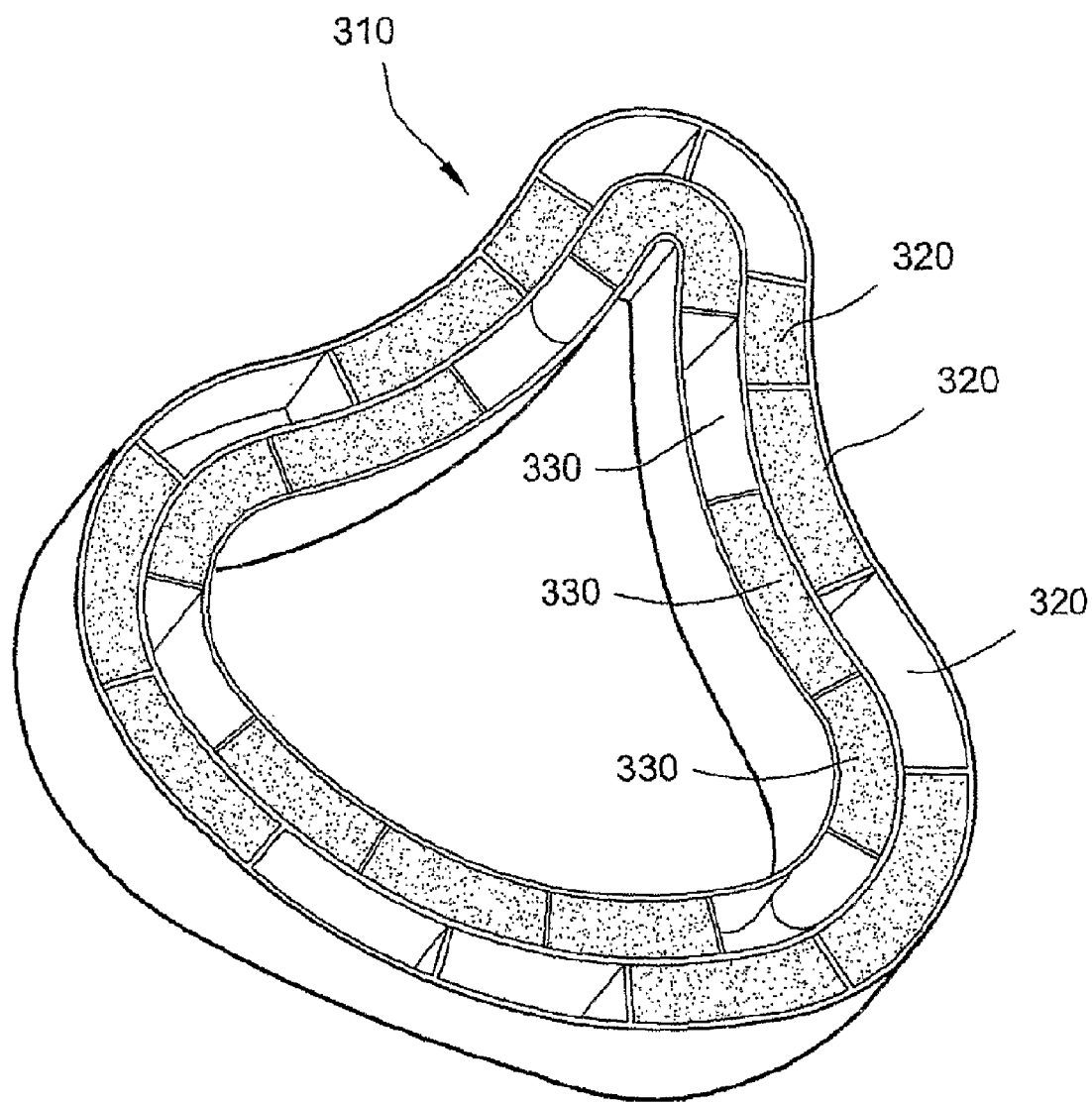
Figure 9:
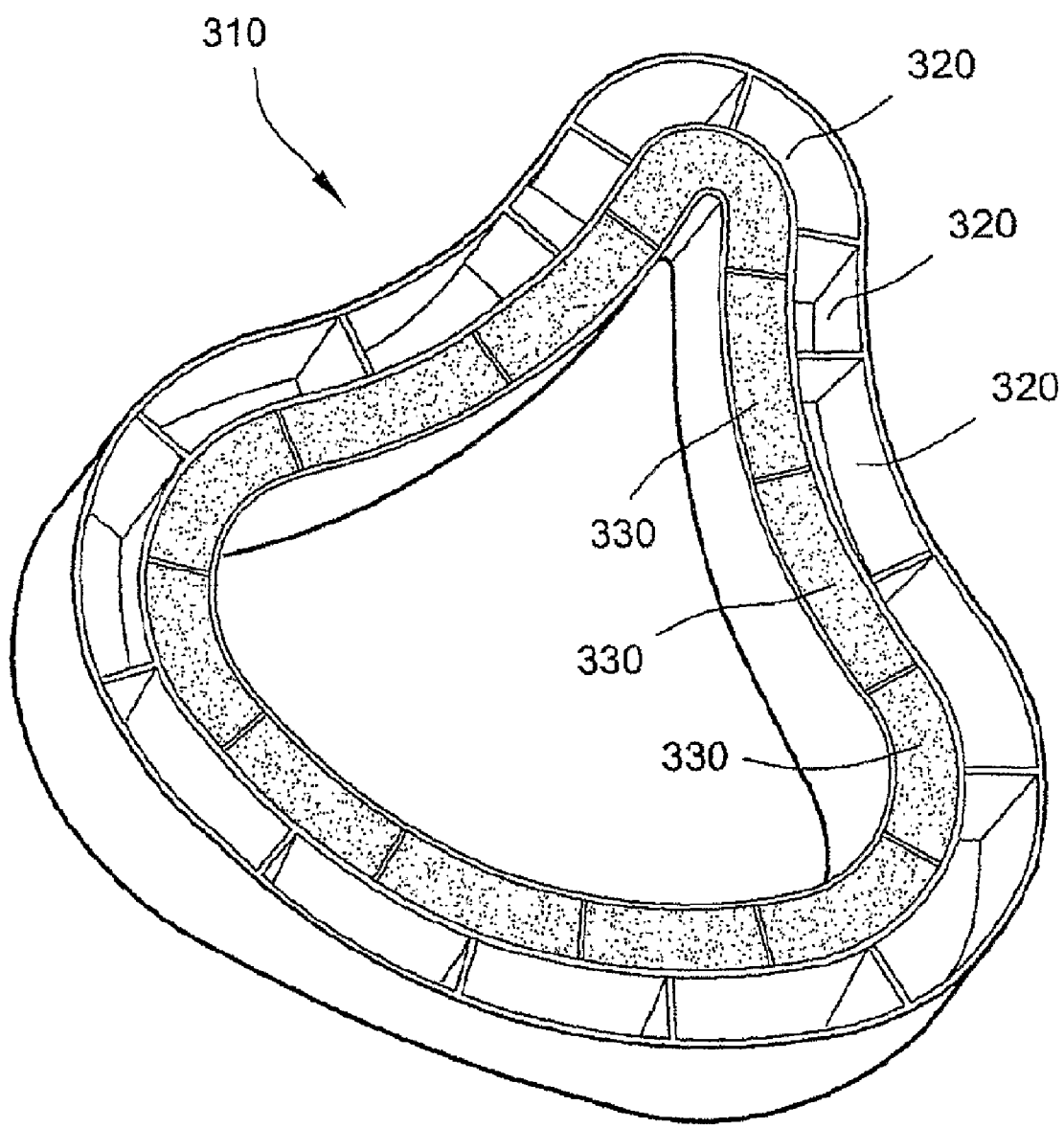
Figure 10:
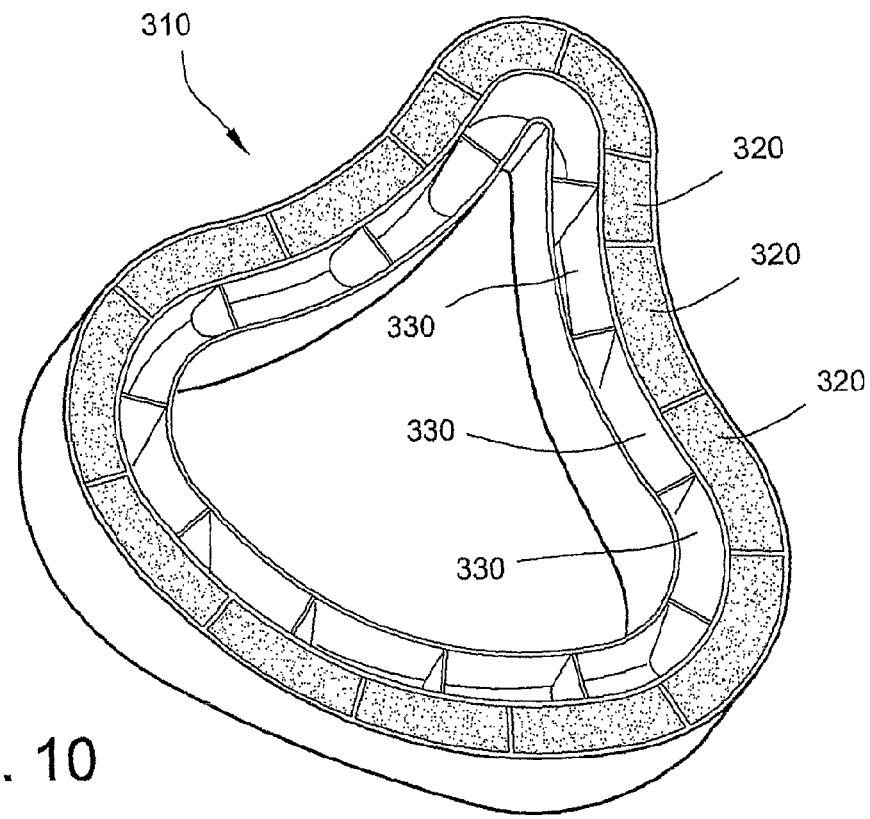

As shown in FIGS. 4 and 5, the partition walls 322, 332 in the cushion 310 may be configured in two ways. Specifically, the partition walls 322, 332 of the bladders 312, 314 may be aligned (as shown FIG. 4), or the partition walls 322, 332 of the bladders 312, 314 may be offset from one another (as shown in FIG. 5). When the partition walls 322, 332 are aligned, the cells 320 of one bladder 312 are aligned with the cells 330 of the other bladder 314. When the partition walls 322, 332 are offset, the cells 320 of one bladder 312 are offset or partially overlap with the cells 330 of the other bladder 314.

This embodiment of the bladder cushion 310 allows the most freedom in applying massage and alternating modes. For example, increasing the number of cells in a bladder will increase the contact pressure variance, and increasing the number of concentric bladders (i.e., the width of the cushion) will increase the contact position variance. Also, by increasing the variance in contact positions, the sealing force may be applied to a larger number of areas. Further, increasing the number of contact areas results in a decrease in the amount of time a force needs to be applied to an area. For example; two concentric bladders results in two areas having pressure applied for 50% of the night, three concentric bladders results in three areas having pressure applied for 33% of the night, and so on. An ideal cushion would have an infinite number of bladders and would cover a large proportion of the patient's face.

2.3.1 Alternating Mode

To ensure that the cushion 310 always maintains a seal, no leak paths are provided at any time. This means that at no time shall there be a cross section of the cushion 310 without an inflated cell 320 or 330. That is, the cells 320, 330 are inflated so that no leak path is provided around the cushion perimeter.

When a cushion 310 with aligned cells 320, 330 is used (FIG. 4), at least one of the aligned cells 320 or 330 is inflated to at least sealing pressure at any one time. During the night, the pressure of the cells 320, 330 may oscillate throughout a range of pressures, and the contact position may oscillate between aligned cells 320 or 330.

When a cushion 310 with offset or overlapping cells 320, 330 are used (FIG. 5), a number of patterns are possible to alternate the contact pressure points or positions. FIGS. 6-10 show various patterns possible with overlapping cells 320, 330. In these figures, the cells 320, 330 filled with stipple represent cells inflated to sealing pressure, and the cells 320, 330 without stipple represent cells deflated to atmospheric pressure. The number of patterns possible is dependant on how many cells are in the cushion. The only restricting factor is that at all times there is a cell inflated to sealing pressure in a cross section of the cushion 310.

In an embodiment, the deflated bladders may be deflated to a pressure below atmospheric pressure (creating suction up the pressure source line). The resulting negative pressure will result in lifting the deflated bladders off the patient's face.

2.3.2 Massage Mode

The massaging effect may be provided in a number of ways, e.g., by altering the contact positions and/or by alternating the contact pressure at a relatively high frequency.

2.3.2.1 Alternating Contact Points Massage

In this mode, the contact points or position of the cushion 310 to the patient will alternate by frequently alternating the inflation and deflation of the cells 320, 330. The contact pressure may be set at sealing pressure.

2.3.2.2 Alternating Contact Pressure Massage

In this mode, all cells 320, 330 will initially be inflated to sealing-pressure. A higher pressure will be identified that is comfortable, and this higher pressure will be determined by how firm a massage is desired by the patient. A lower than sealing pressure will also be identified, e.g., by default this will be atmospheric pressure. However, as noted above, the lower than sealing pressure may be below atmospheric pressure to lift the deflated bladders off the patient's face. The pressures of the cells 320, 330 will then oscillate between the low and high pressure limits.

2.3.2.3 Combination of Alternating Contact Pressures and Points Massage

This massage mode will be set up so that a pattern of cells is doing the massage, and the other cells are deflated. This massage mode may provide the greatest freedom to design the most relaxing massage. As with contact points massage, the only restriction is that at all times in a cross-section, there will be a cell inflated to at least sealing-pressure. This means that contact pressure and contact positions can be oscillating dependently or independently of each other resulting in a more soothing massage.

2.4 Single Bladder Cushion

Figure 11:
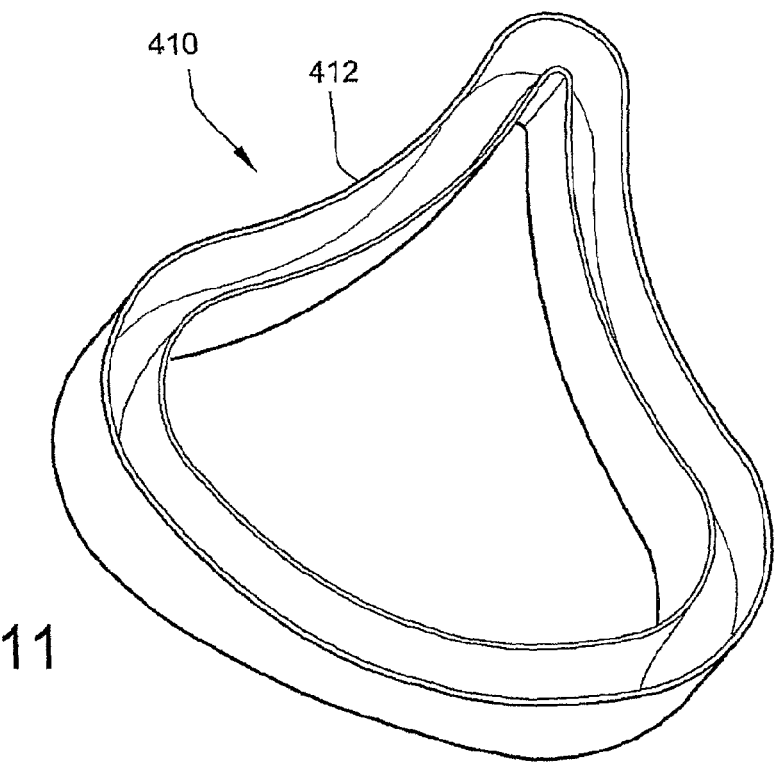
FIG. 11 is a perspective view of a bladder cushion for a patient interface according to another embodiment of the present invention.

FIG. 11 illustrates a cushion 410 including a single bladder 412. In use, the bladder 412 may be pressurized to provide a seal with the patient's face. This is the simplest of the bladder cushion designs. With this design, the contact pressure is the only parameter that may be controlled. As a result, alternating mode may not be as effective as there will always be at least sealing pressure in the bladder 412.

3 Bladder Forehead Cushions

Similar to the cushions described above, one way to control the contact pressures and contact locations at the forehead support is to use fluid-filled bladders as forehead cushions, e.g., air bladder forehead cushions. The forehead support design may include one large cushion, or two or more smaller cushions.

3.1 Horizontally or Vertically Partitioned Bladder Forehead Cushion

The forehead cushion may be divided into multiple bladders or cells. In use, the bladders may be pressurized independently from one another.

In the illustrated embodiment, the bladders of the forehead cushion are divided into aligned bladders along an orientation. This orientation may be horizontal, vertical, or any other suitable orientation.

Figure 12:
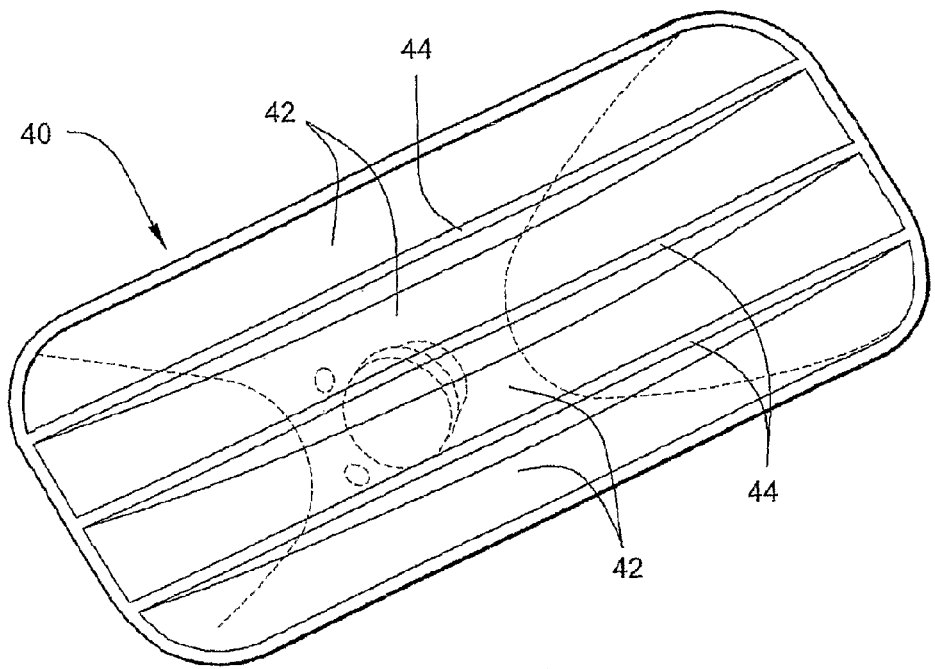
FIGS. 12-14 illustrate a bladder forehead cushion for a patient interface according to an embodiment of the present invention.
Figure 13:
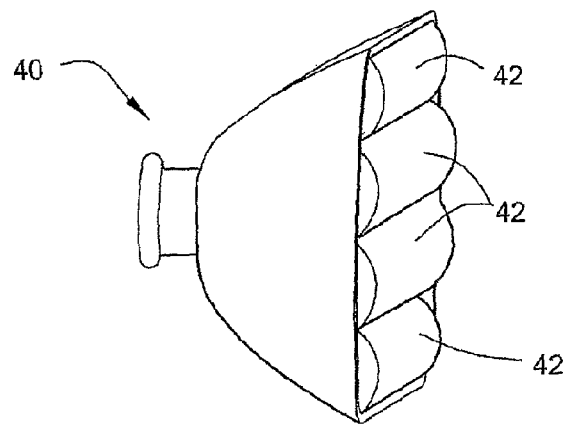
Figure 14:
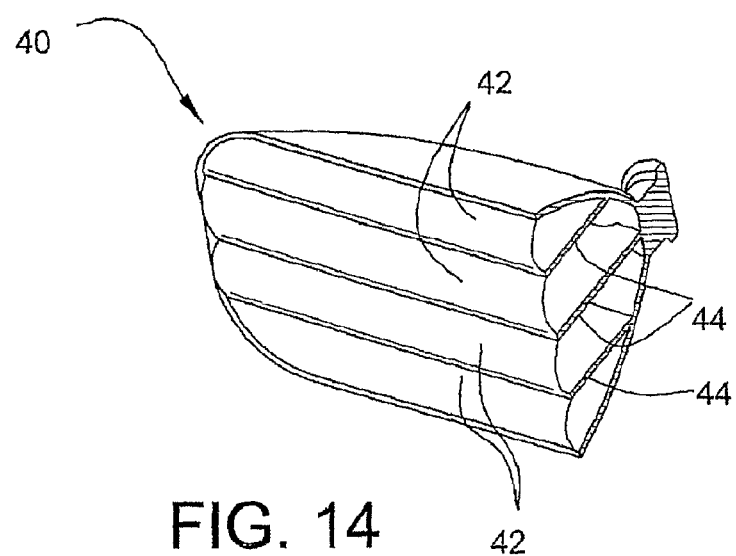
Figure 15:
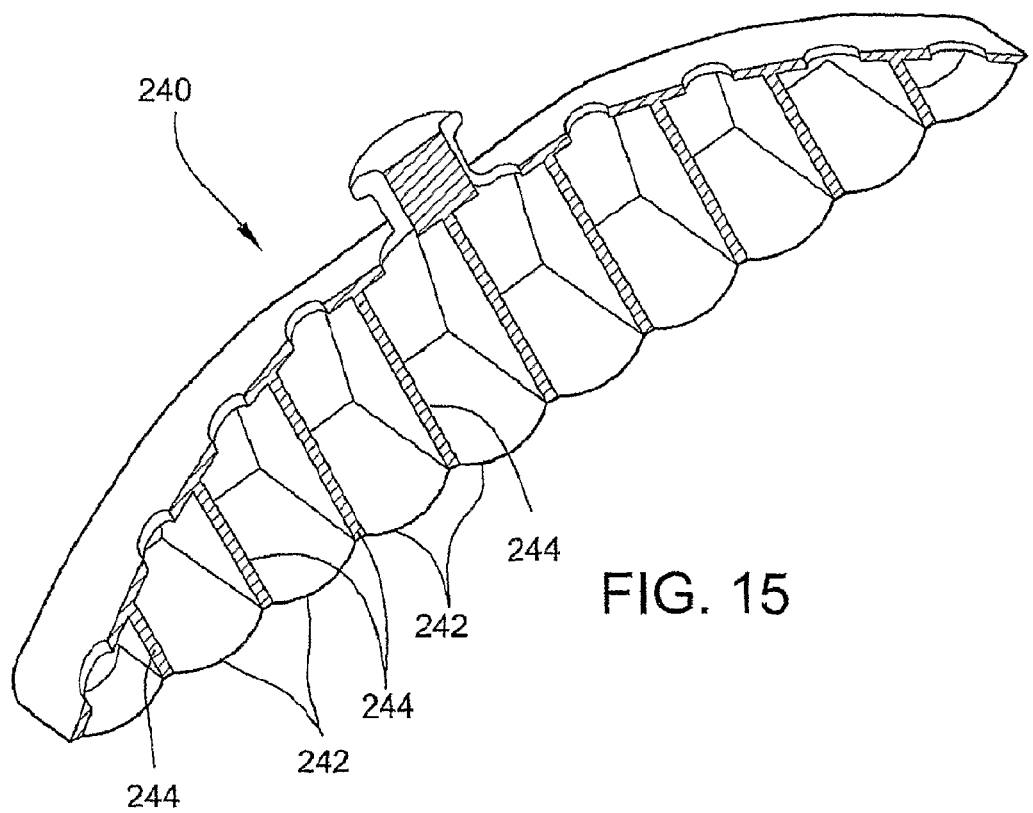
FIG. 15 is a cross-sectional view of a bladder forehead cushion for a patient interface according to another embodiment of the present invention.

For example, FIGS. 12-14 illustrate a forehead cushion 40 divided into multiple bladders 42, e.g., four bladders, by partition walls 44. As illustrated, the bladders 42 and partition walls 44 thereof are oriented generally horizontally in use. FIG. 15 illustrates a forehead cushion 240 divided into multiple bladders 242, e.g., ten bladders, by partition walls 244. As illustrated, the bladders 242 and partition walls 244 thereof are oriented generally vertically in use.

Both styles of forehead cushion 40, 240 can operate in a similar manner. That is, the forehead cushions 40, 240 may operate in alternating or massage mode to alternate the contact pressure and/or contact position of the cushions 40, 240.

3.1.1 Alternating Mode

In alternating mode, at least one bladder 42, 242 will be inflated to a pressure that feels comfortable to the patient at the beginning of the night. If there are any rigid sections in the forehead support, the pressure will be sufficient to allow the forehead cushion 40, 240 to lift these sections off the patient's forehead. This pressure will be identified as the default pressure. If the headgear is not adjustable, or is not adjusted from night to night, then the default pressure will always remain the same. Throughout the night, the bladders 42, 242 will inflate to the default pressure, and deflate to atmospheric pressure. However, it may be desirable to deflate the bladders 42, 242 to a pressure that is less then the default pressure but higher then atmospheric pressure. It is also possible to deflate one or more of the bladders to a pressure below atmospheric pressure so that the resulting negative pressure lifts the bladders off the patient's forehead. To reduce the pressure at an isolated area, the force may be distributed over a larger area. Further, the default pressure may be reduced if some force is still applied by the other lower pressurized bladders. In use, at least one of the bladders 42, 242 is always pressurized to the default pressure. This arrangement prevents any rigid sections of the forehead support from contacting the patient's forehead.

3.1.2 Massage Mode

Massage mode operates in a similar manner as alternating mode with the exception that the bladders 42, 242 may be inflated to a higher pressure than the default pressure. This higher pressure will be set before use and will be determined by how firm a massage the patient wishes. The bladders 42, 242 may also be deflated to a pressure higher than atmospheric pressure and lower than the default pressure. This pressure will be determined by the patient's preference. The massaging functionality could also be achieved by a percussion vibration device. The device could operate by rotation of an unbalanced mass or vibration of a mass by other means.

3.2 Horizontally and Vertically Partitioned Bladder Forehead Cushion

Figure 16:
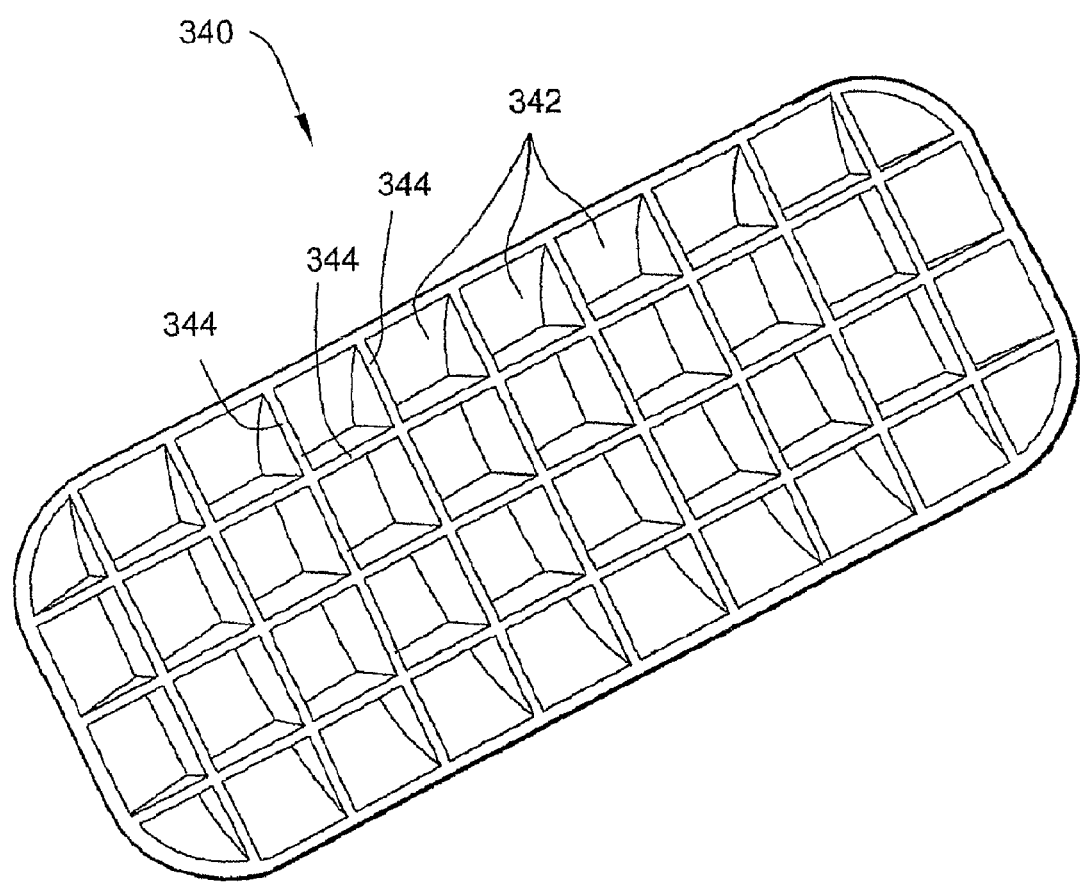
FIG. 16 is a perspective view of a bladder forehead cushion for a patient interface according to another embodiment of the present invention.

FIG. 16 illustrates a forehead cushion 340 divided into multiple bladders or cells 342 by partition walls 344 that extend both horizontally and vertically. In use, the cells 342 may be pressurized independently from one another. This arrangement allows the greatest control of forehead cushion to skin contact. The forehead cushion 340 may operate in a similar manner to the forehead cushions described above, e.g., in alternating or massage mode, to alternate the contact pressure and/or contact position of the forehead cushion 340 in both horizontal and vertical axes.

3.3 Single Bladder Forehead Cushion

Figure 17:
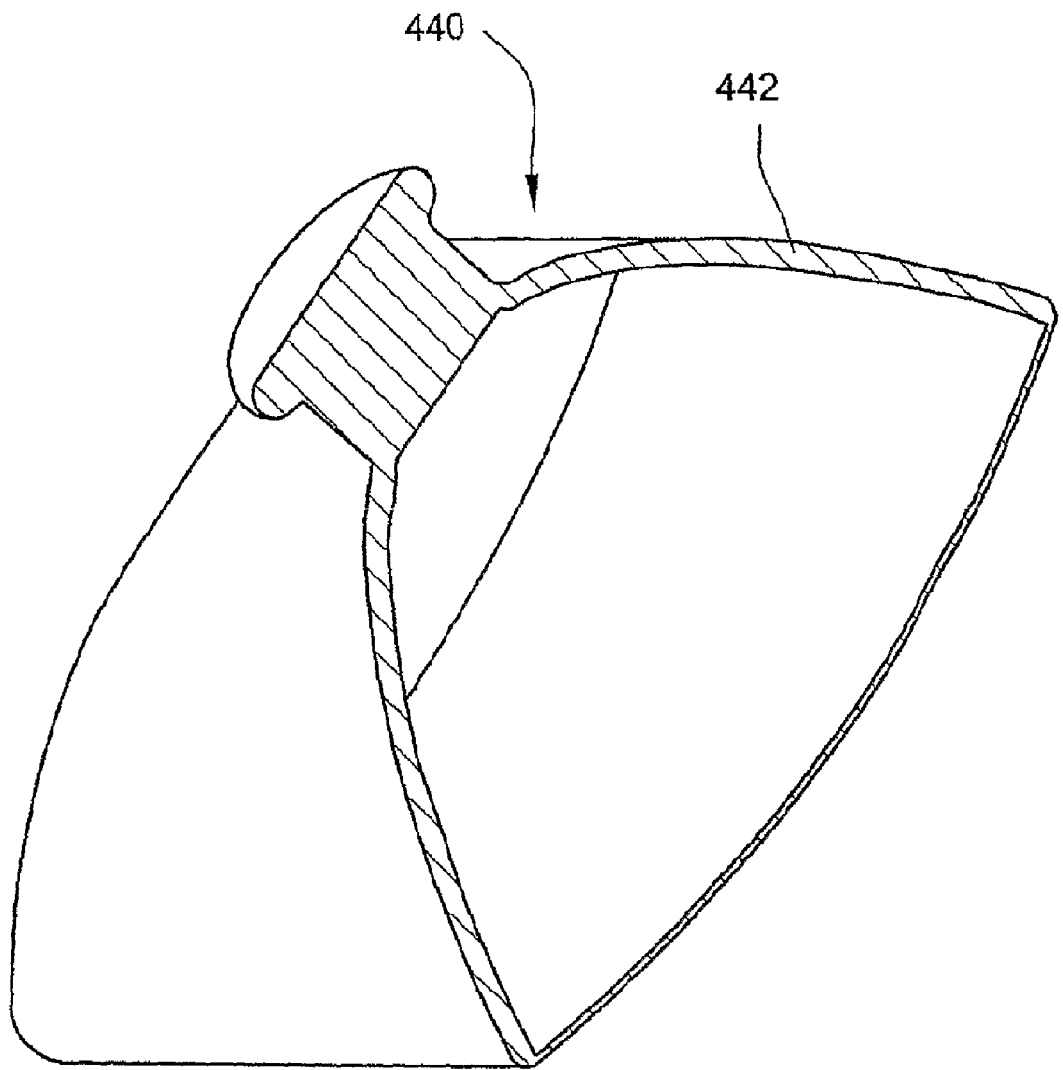
FIG. 17 is a perspective view of a bladder forehead cushion for a patient interface according to another embodiment of the present invention.

FIG. 17 illustrates a forehead cushion 440 including a single bladder 442. In use, the bladder 442 may be pressurized to engage the patient's forehead. This is a simpler design of the bladder forehead cushion. With this design, the contact pressure is the only parameter that may be adjusted. As a result, this forehead cushion 440 may only operate in a massage mode, wherein the forehead cushion 440 is initially inflated to default pressure, and then the pressure will be oscillated between the default pressure and a higher set pressure. By adjusting the pressure magnitude and the forehead cushion's location on the patient's forehead, the fit of the mask may also be adjusted. For example, a higher pressure will push the forehead support further from the patient's face resulting in the mask tilting into position.

4. Bladder Headgear Straps

Similar to the cushions described above, one way to control the contact pressures and contact locations at the headgear is to use fluid-filled bladders in the headgear, e.g., air bladder headgear. The headgear is designed with at least two elements. At least one element will take the strain of the mask, and another element will provide a cushion between the headgear and the patient's head. This cushion area is where the bladder is positioned. In an embodiment, the headgear includes bladder straps, e.g., air bladder straps, that are structured such that that inflating or deflating the straps will not effect the tension on the mask, i.e., manipulating pressures in the straps will not pull or push the mask off the patient's face which can lead to discomfort or leaks. Also, the bladder headgear may be used to raise sharp edges of the headgear away from the patient's skin.

Figure 18:
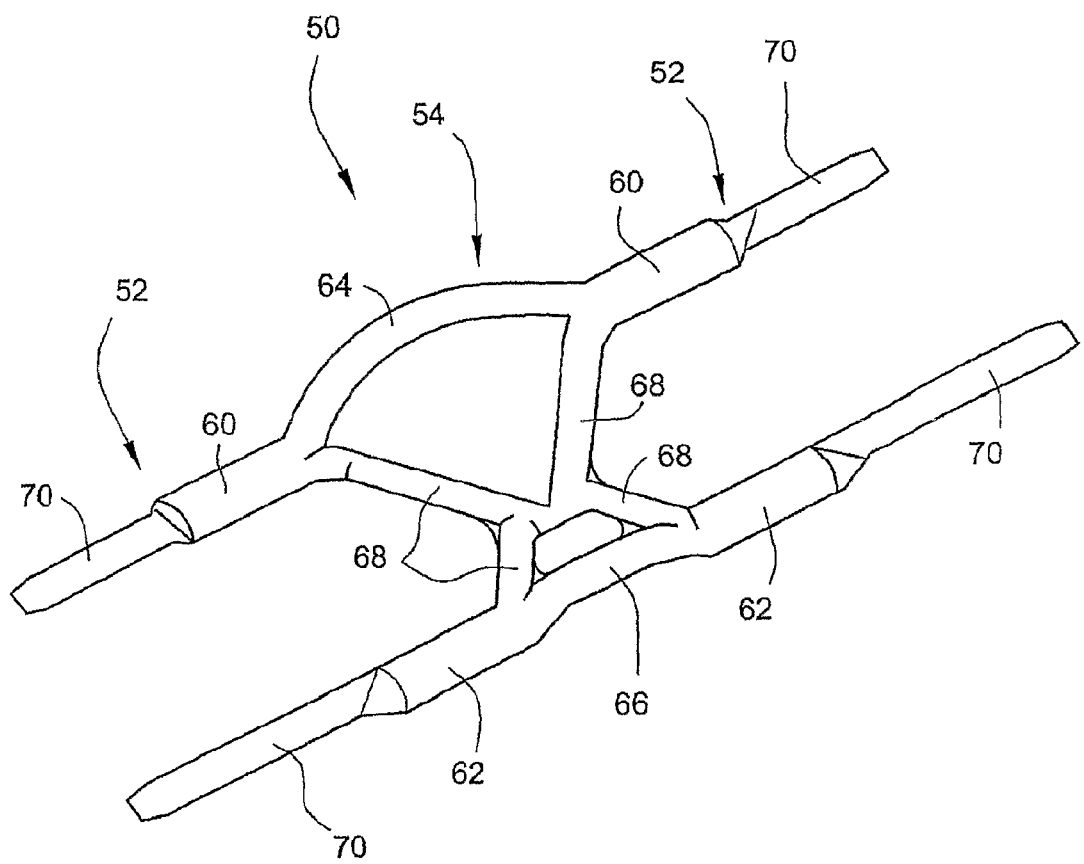
FIG. 18 is a perspective view of bladder headgear according to an embodiment of the present invention.

FIG. 18 illustrates bladder headgear 50, e.g., air bladder headgear, according to an embodiment of the present invention. As illustrated, the headgear 50 includes fluid-fillable bladders as straps. In use, the bladders may be pressurized independently from one another.

Specifically, the headgear includes two side portions 52 with a rear portion 54 connecting the side portions 52. Each side portion 52 comprises an upper side strap 60 and a lower side strap 62. The rear portion 54, which interconnects the two side portions 52, includes a curved upper strap 64, a lower strap 66, and intermediate connecting straps 68 extending between the curved upper strap 64 and the lower strap 66. The connecting straps 68 are inclined with respect to the curved upper strap 64 and the lower strap 66. As illustrated, each of the upper side straps 60, lower side straps 62, curved upper strap 64, lower strap 66, and connecting straps 68 are in the form of fluid-fillable bladders.

In the illustrated embodiment, fastening of the upper and lower straps 60, 62 to the patient interface may be assisted by use of a hook and loop material, such as VELCRO®. For example, the free end of each upper and lower strap 60, 62 may include a strip of hook material 70 attached thereto. The upper and lower straps 60, 62 may include a portion of loop material that engages the strip of hook material 70 when the upper and lower straps 60, 62 are connected to the patient interface. However, the upper and lower straps 60, 62 may be connected to the patient interface in any other suitable manner, e.g., locking clips.

4.1 Multi-Channeled Headgear

In an embodiment, the bladder headgear 50 may be divided into two or more channels. For example, each of the bladder straps 60, 62, 64, 66, 68 may be pressurized independently from one another. Alternatively, the bladder straps 60, 62, 64, 66, 68 may be selectively grouped into two or more groupings or channels.

4.1.1 Alternating Mode

In alternating mode, at least one of the channels is inflated to a pressure that is sufficient to lift the headgear off the patient's head. That is, at least one channel is inflated so that no part of the element that is designed to take the strain of the mask is in contact with the patient's head. This arrangement does not allow this element (which becomes rigid under strain) to cause irritation when against the patient's head. Throughout the night, the channels will be inflated to the default pressure and deflated to atmospheric pressure. However, the deflated channels may be deflated to a pressure below atmospheric pressure (creating suction up the pressure source line). The resulting negative pressure will result in lifting the deflated channels off the patient's head. This arrangement alternates or moves the contact position in use. At least one channel is always inflated to the default pressure so that headgear straps will not drop from the patient's head.

4.1.2 Massage Mode.

As with alternating mode, at least one channel is always inflated to the default pressure in massage mode. However, a higher set pressure and a lower set pressure will be set. The pressures in the channels will then be oscillated between these high and low limits.

4.2 Partitioned Bladder Headgear

In another embodiment, the bladder headgear may include at least one channel that is partitioned into multiple cells. For example, at least one of the bladder straps 60, 62, 64, 66, 68 may include multiple cells that can be pressurized independently from one another.

The cells may be structured such that the contact position of the headgear may be manipulated. All the cells may not necessarily be the same size, but they will be positioned so that some of the cells can be deflated without the headgear contacting the patient's skin. For example, each cell may be relatively small and its dimension may be determined by the curvature of the patient's head. The cells may be larger on flat sections of the patient's head and may be smaller on curved sections of the patient's head. The cell length may be in proportion to the curvature and to the thickness of the bladder.

The word "headgear" as used above includes any security portions adapted to contact a patient's face, cheeks, head, or neck, etc.

4.2.1 Alternating Mode

In alternating mode, patterns of cells will be identified that will lift the headgear off the patient's head when inflated. These patterns will then be alternated throughout the night.

4.2.2 Massage Mode

Massage mode may operate similar to alternating mode but at a higher frequency. Alternatively, all the cells may be inflated and the pressures oscillated.

4.3 Partitioned Multi Channeled Headgear

In another embodiment, the bladder headgear may operate as a multi-channeled headgear and a partitioned bladder headgear. For example, each of the straps may include a separate bladder, and each bladder may include multiple cells that can be pressurized independently from one another.

5. Bladder Headgear Cap

A bladder headgear cap, e.g., air bladder headgear cap, may be provided to replace traditional headgear with a cap. In an embodiment, the bladder headgear cap includes multiple bladders that may be partitioned by one or more partition walls. The bladder headgear cap may operate in a similar manner as the multi channeled headgear, except that there may be more freedom of the alteration of pressure contact positions; As with the above-described headgear, inflation and deflation of the bladder headgear cap does not result in altering the tension in the headgear.

6. Bladder Chinstrap

A bladder chinstrap, e.g., air bladder chinstrap, may be provided to add additional support. In an embodiment, the bladder chinstrap may include at least one bladder, e.g., air bladder, that can be inflated or deflated. As with the above-described headgear, adjusting the pressures of the bladders does not result in altering the tension in the chinstrap. Partitioning of the bladders is also possible, and may allow more freedom in adjusting pressure contact positions. The pressurizing of the bladder chinstrap may be used to modify the headgear tension and to seal leaks by moving the mask vertically on the patient's face.

7. Pressure Control

The pressure, e.g., air pressure, applied to bladders of the cushions, forehead cushions, headgear, caps, and chinstraps described above may be controlled in use.

7.1 Constant Pressure Source with Release Valve

In an embodiment, the pressure may be controlled by a motor having a constant motor speed or flow and a release valve on the delivery line that taps off some of the pressure. By controlling the diffuser flow through this release valve, the pressure being delivered to the bladders may be controlled.

7.2 Variable Pressure Source

In another embodiment, the pressure source may monitor the pressure being delivered to the bladders, and adjust the motor speed accordingly to control the pressure being delivered. In this way, a closed control loop is provided by a pressure sensor in communication with a motor speed adjustment device. In an alternative embodiment, pressure can be adjusted by the motor accessing a simple pre-prepared look-up table.

8. Pressure Position Control

The location or position of pressure, e.g., air pressure, being applied to bladders of the cushions, forehead cushions, headgear, caps, and chinstraps described above may be controlled in use. That is, devices may be provided to determine which bladders or which cells in a particular bladder receive pressure during use.

8.1 Distributor On or Near the Mask

Figure 19:
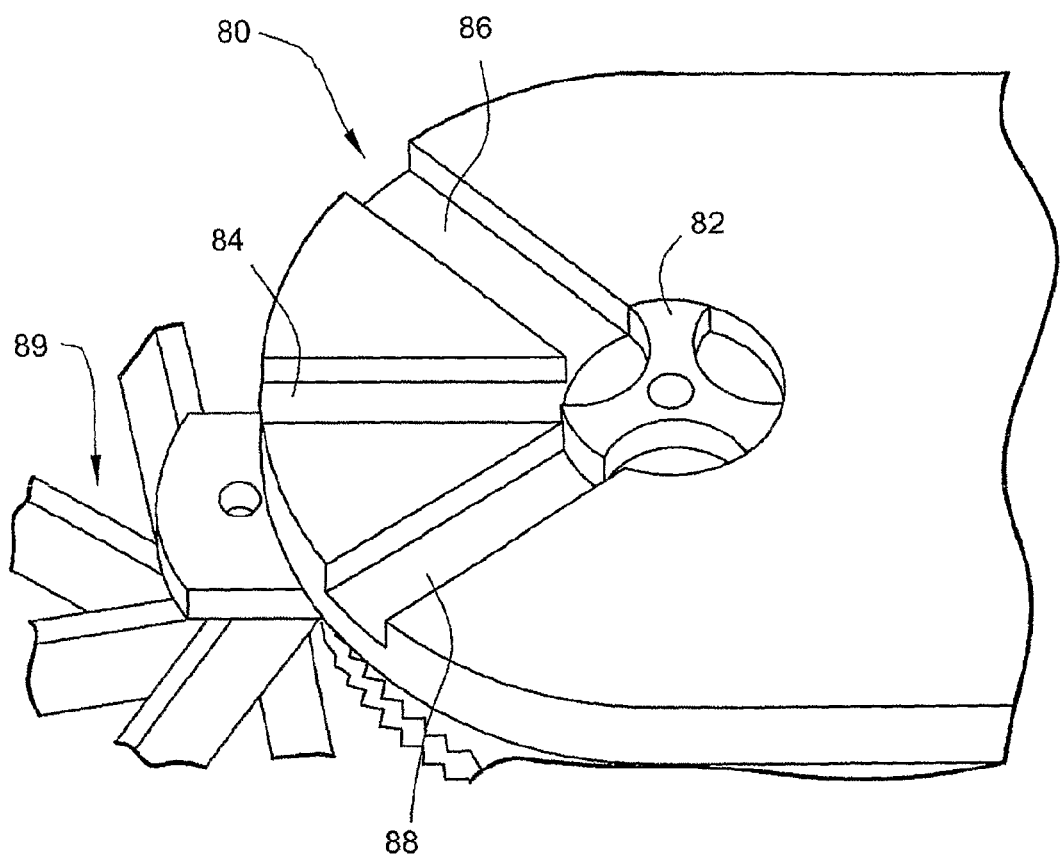
FIGS. 19-20 are perspective views of an pressure distributor according to an embodiment of the present invention.
Figure 20:
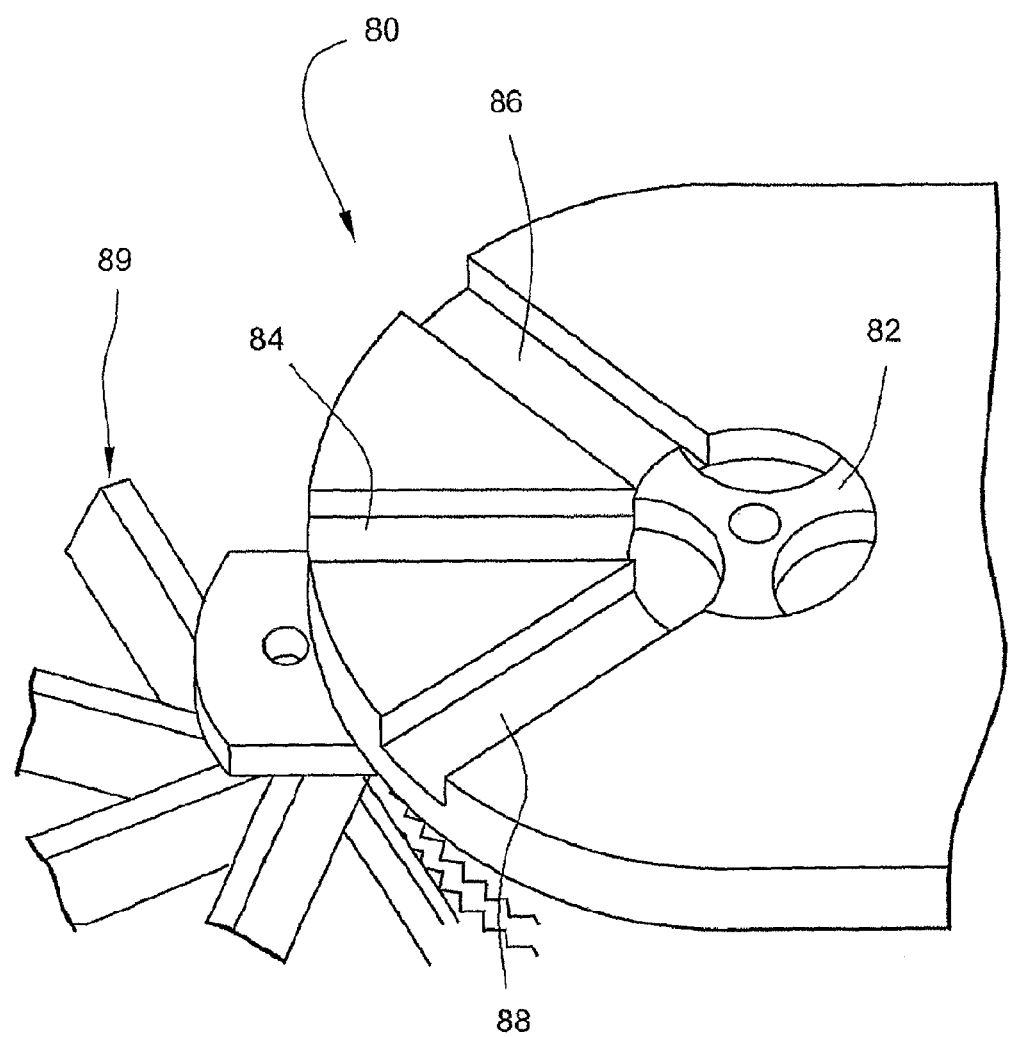

FIGS. 19 and 20 illustrate an pressure position control device or pressure distributor 80, e.g., air pressure distributor, according to an embodiment of the present invention. The device 80 is preferably mounted on the mask frame, but may be located near the mask.

The device 80 includes a rotating distributor wheel 82, conduits 84, 86, 88 to receive and deliver pressure, and a power source. In the illustrated embodiment, the center conduit 84 receives pressure from an external source, and the two other conduits 86, 88 deliver the pressure to different cells of the bladder. The partitioning of the distributor wheel 82 is arranged so that the distance between cut-outs is less than a width of the pressure supply conduit 84. This arrangement ensures that at all times at least one conduit 86, 88 is receiving pressure. Both conduits 86, 88 will receive pressure for a brief amount of time, i.e., the overlap time. The distributor wheel 82 rotates to select which conduits 86, 88 will receive pressure. It should be understood that the number of different cells being controlled may be increased. For example, the conduits 84, 86, 88 may be mirrored onto the right hand side of the distributor wheel 82. In this arrangement, the distributor wheel 82 would control two sets of conduits with two different pressure sources. The speed of the distributor wheel 82 is determined by the desired alternating speed.

Power may be applied to the device 80 by a number of methods. For example, power may be applied by a low impedance impeller 89 (as shown in FIGS. 19 and 20) that is driven by the diffuser flow of the mask or the flow from the flow generator. Alternatively, power may be applied by a winding mechanism (e.g., similar to a clock), an electric motor, etc. A timing circuit may be used to control the rotation speed.

8.2 Distributor at the Pressure Source

A distributor, such as the one described above in FIGS. 19 and 20, may be provided at the pressure source, e.g., flow generator, to control pressure position.

8.3 Selector Valve

In another embodiment, a selector valve may be used at the mask to select which bladders or cells receive pressure. The selector valve includes at least one input line and at least two output lines. A single input or output may be selected, or multiple inputs or outputs may be selected at once, e.g., two outputs may receive pressure from one input.

8.3.1 One to Many Selector Valve

Figure 21:
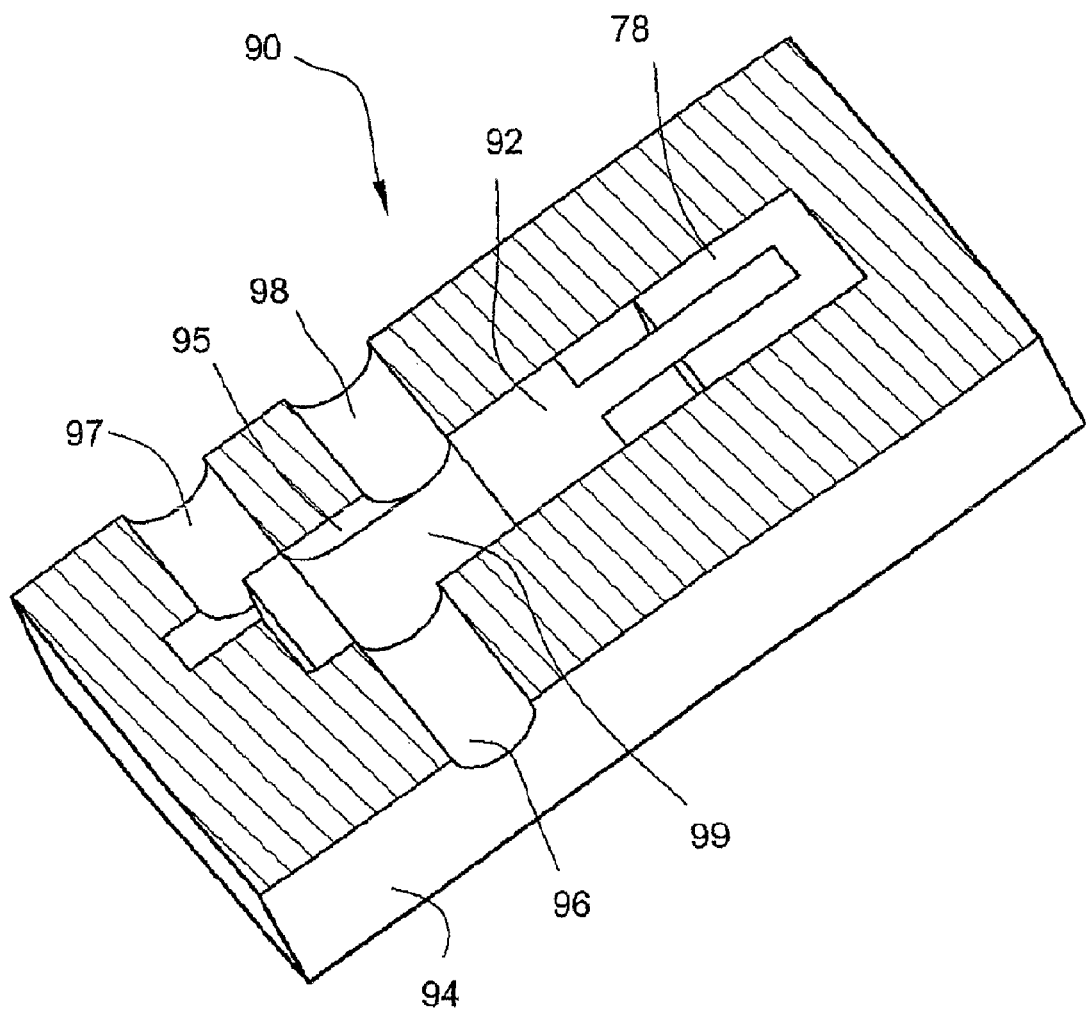
FIG. 21 is a cross-sectional view of a selector valve according to an embodiment of the present invention.

FIG. 21 illustrates a selector valve 90 according to an embodiment of the present invention. As illustrated, the selector valve 90 is a one to many selector valve that includes one input and multiple outputs, e.g., two outputs. In the arrangement, only one cell pressure is achievable as all the cells when selected will have the same pressure supplied by the pressure source. The pressure source may vary the pressure, but the selector valve 90 cannot.

In the illustrated embodiment, the selector valve 90 includes a slider 92 and a housing 94 having a slot 95 for receiving the slider 92. One hole 96 is provided on one side of the slot 95, and two holes 97, 98 are provided on the other of the slot 95. The slider 92 has a rectangular cut-out 99 that is large enough to cover two adjacent holes. This arrangement means that the cut-out 99 will create a channel between the holes 96 to 97 or 96 to 98 on either side of the slot 95. To select which of the two holes 97, 98 on one side is connected to the hole 96 on the other side, the slider 92 simply slides or moves within the slot 95.

The selector valve 90 also includes a drive 78 for driving the slider 92. The drive 78 may be any suitable actuating device to control slider movement, e.g., solenoid, pneumatic piston, servo-motor, etc. The illustrated selector valve 90 may act as a one to two valve or as a two to one valve wherein the valve 90 includes two pressure source lines in and one supply line out.

Figure 22:
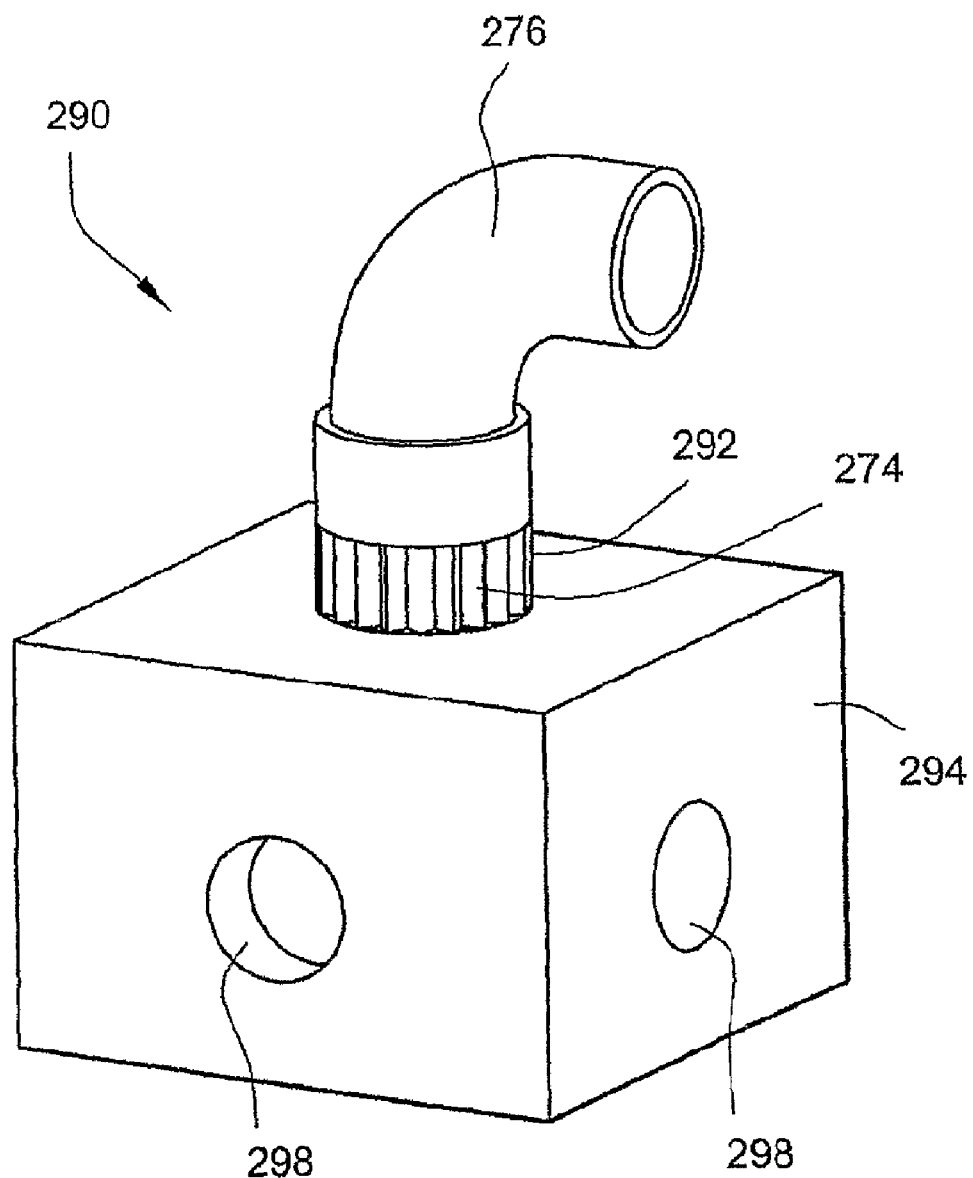
FIGS. 22-23 illustrate a selector valve according to another embodiment of the present invention.
Figure 23:
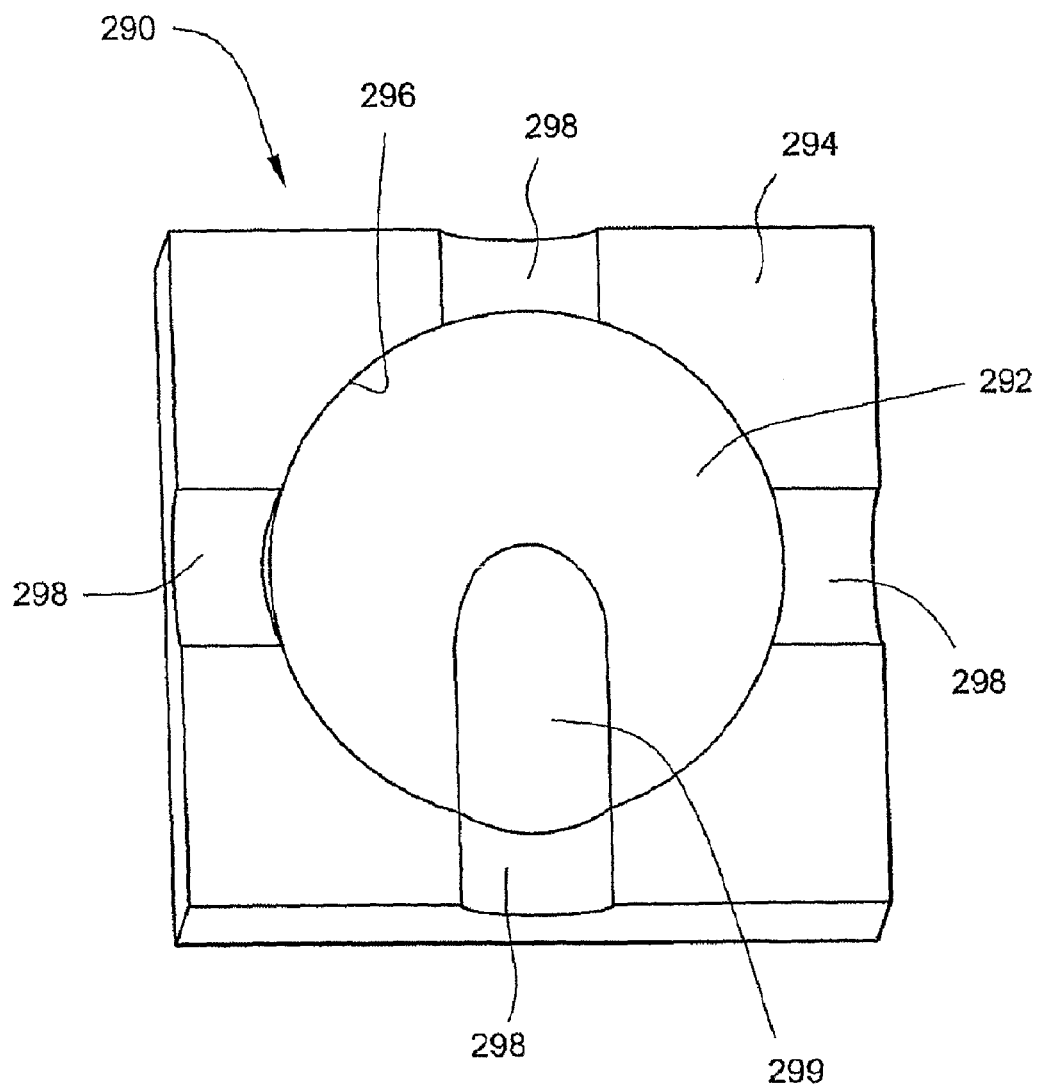
Figure 24:
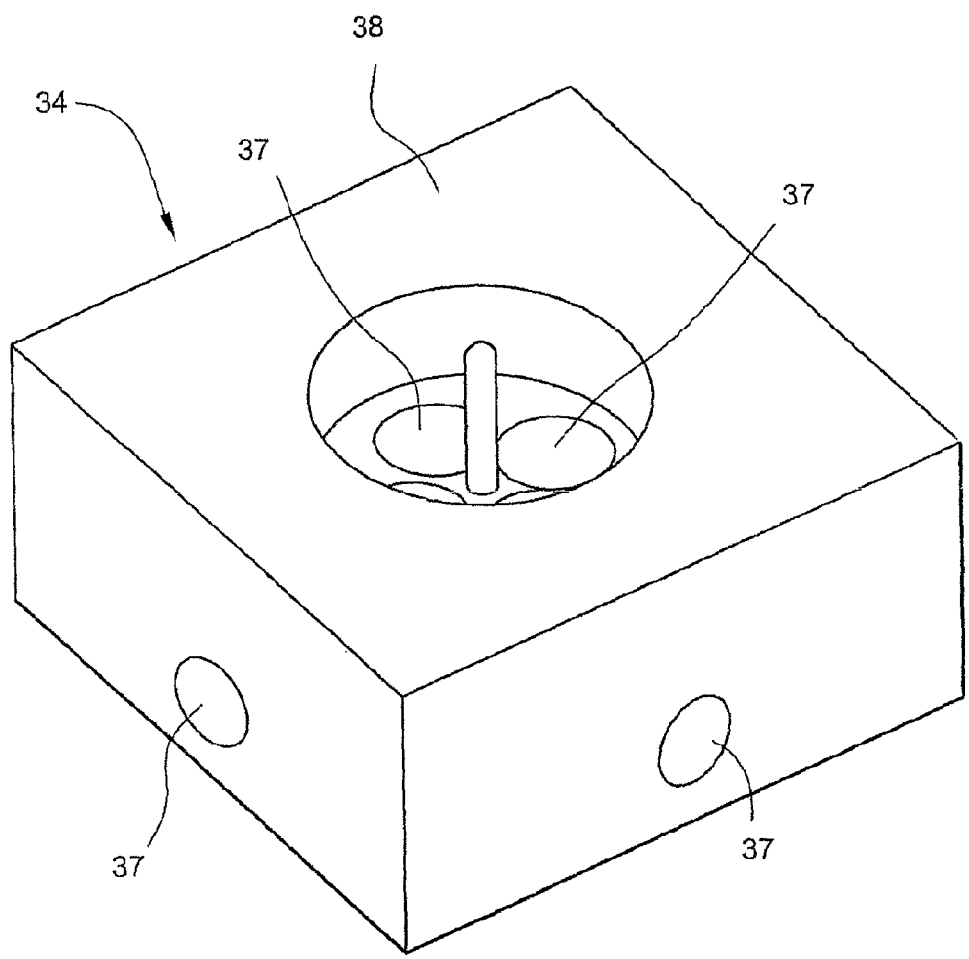
FIGS. 24-27 illustrate a pressure release according to an embodiment of the present invention.
Figure 25:
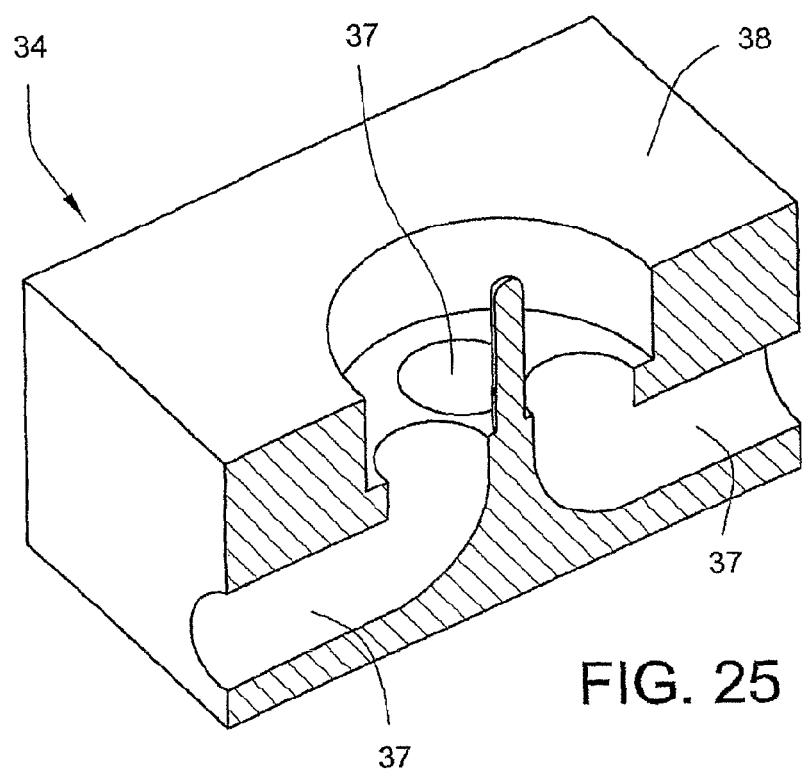
Figure 26:
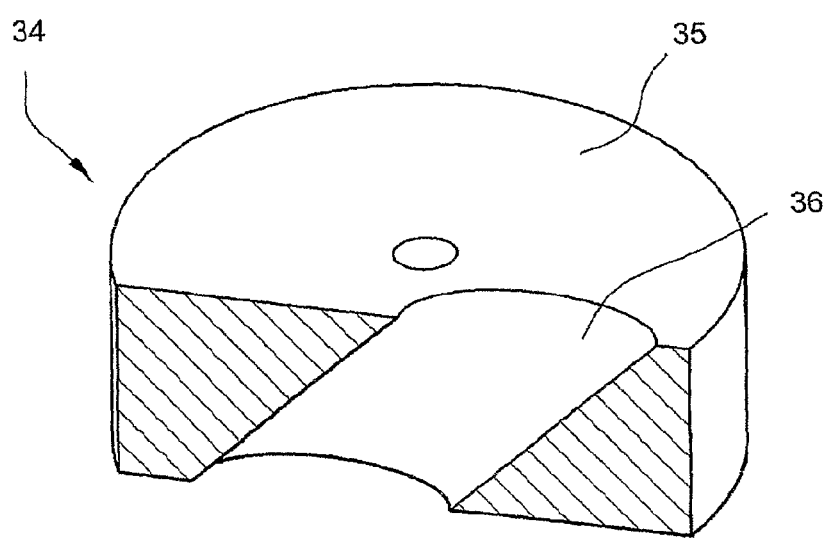
Figure 27:
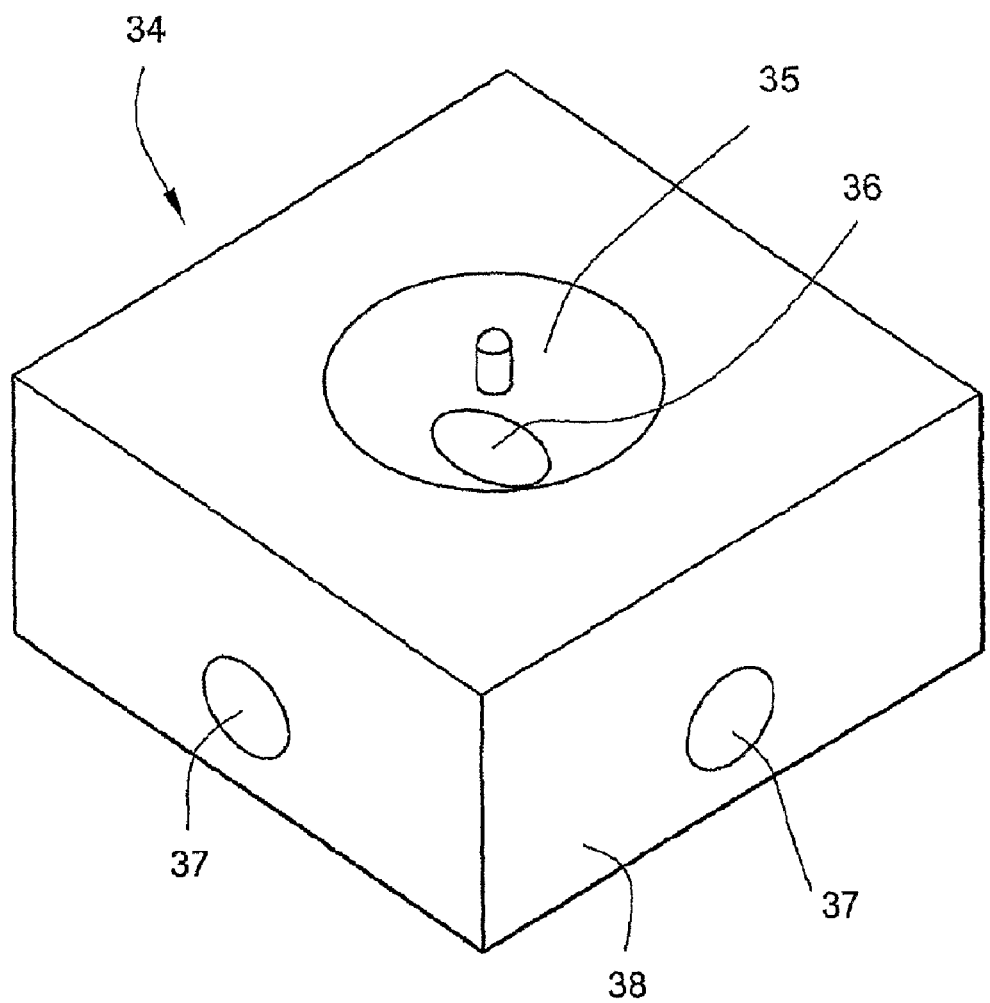

FIGS. 22 and 23 illustrate a selector valve 290 according to another embodiment of the present invention. As illustrated, the selector valve 290 is a four to one (or one to four) selector valve.

As illustrated, the selector valve 290 includes a rotating selector 292, a housing 294, a swivel elbow 276, and a driving mechanism. The housing 294 has a circular cut-out 296 to hold the rotating selector 292. Holes 298, e.g., four holes, are provided around the circumference of the cut-out 296, and oriented generally normal to the circumference of the cut-out 296. The rotating selector 292 has a channel 299 that starts along its axis and then bends about 90 degrees. The bend is along its radius and is oriented to line up with the holes 298 in the housing 294 (as best shown in FIG. 23). The elbow 276 is attached to the top of the rotating selector 292. The elbow 276 is free to swivel which allows the rotating selector 292 to move with respect to the elbow 276. In use as a one to four selector valve, the elbow 276 is connected to a pressure Source and pressure is fed into the rotating selector 292 that is rotated to line up with one of the four holes 298 in the housing 294. The driving mechanism, e.g., a stepper motor, is used to rotate the rotating selector 292, e.g., via gear teeth 274 provided on the rotating selector 292.

8.3.2 One to Many Selector Valve with Pressure Release

In an embodiment, a selector valve may be configured such as those described above in FIGS. 21-23, but each outlet will have a vent to atmosphere or to the mask. In this arrangement, the flow coming out of each outlet may be tuned by adjusting the diffuser flow through each vent. As a result, the cells will not be restricted to having the same pressure.

8.3.3 Many to Many Selector Valve

In another embodiment, the selector valve may be a many to many selector valve having multiple inputs and multiple outputs. This arrangement enables the bladders or cells to alternate between the pressures that are input to the valve. As a result, each output can be supplied with the pressure from any of the inputs or no pressure at all. The more inputs allows a larger range of pressures. In an embodiment, the many to many selector valve includes two inputs, however any number of inputs is possible.

8.4 Impeller Pressure Release

In an embodiment, the control method may use pressure release to dip the pressure automatically. The pressure source to the bladders or cells will provide constant flow (i.e., the flow will be controlled, not the pressure). FIGS. 24-27 illustrate an impeller pressure release 34 that includes an extra conduit leading from a cell or input conduit to a cell in a housing that will control a spinning orifice. In the illustrated embodiment, the housing of the pressure release 34 allows four cells to be controlled.

To control the pressure drop, a spinning cover 35 (cross-section shown in FIG. 26) with an offset hole 36 is placed on top of the conduits 37 in the housing 38. Only one conduit 37 will be in line with the hole 36 in the spinning cover 35 at any time. The spinning cover 35 will be free to rotate about a center axis since the hole is offset. The flow of the fluid escaping to atmosphere through the hole 36 will force the spinning cover 35 to rotate.

8.5 Low Impedance Impeller

In another embodiment, a low impedance impeller may be located at the diffuser vent on the mask, on the hose from the flow generator, or on an orifice from the hose. The impeller may be structured to drive other control mechanisms, e.g., distributor, selector valve, etc.

9. Algorithms for Controlling Bladders

Algorithms may be provided to control the pressure being applied to bladders of the cushions, forehead cushions, head gear, caps, and chinstraps described. The algorithms may be designed to correct leak.

9.1 Leak Correction

Leak correction may be achieved manually or automatically. FIGS. 28-31 illustrate algorithms or methods for correcting leak automatically. However, leak may be corrected manually, and be used to provide a custom fit of the mask. For example, cells or bladders may be selected by the patient/clinician, and their pressure can be set. This information will be stored and be used as the set pressure for the bladders or cells. This manual control may be used at startup to set the pressure on a night to night basis, or may be set at purchase by a clinician.

9.1.1 Single Bladder Cushion

Figure 28:
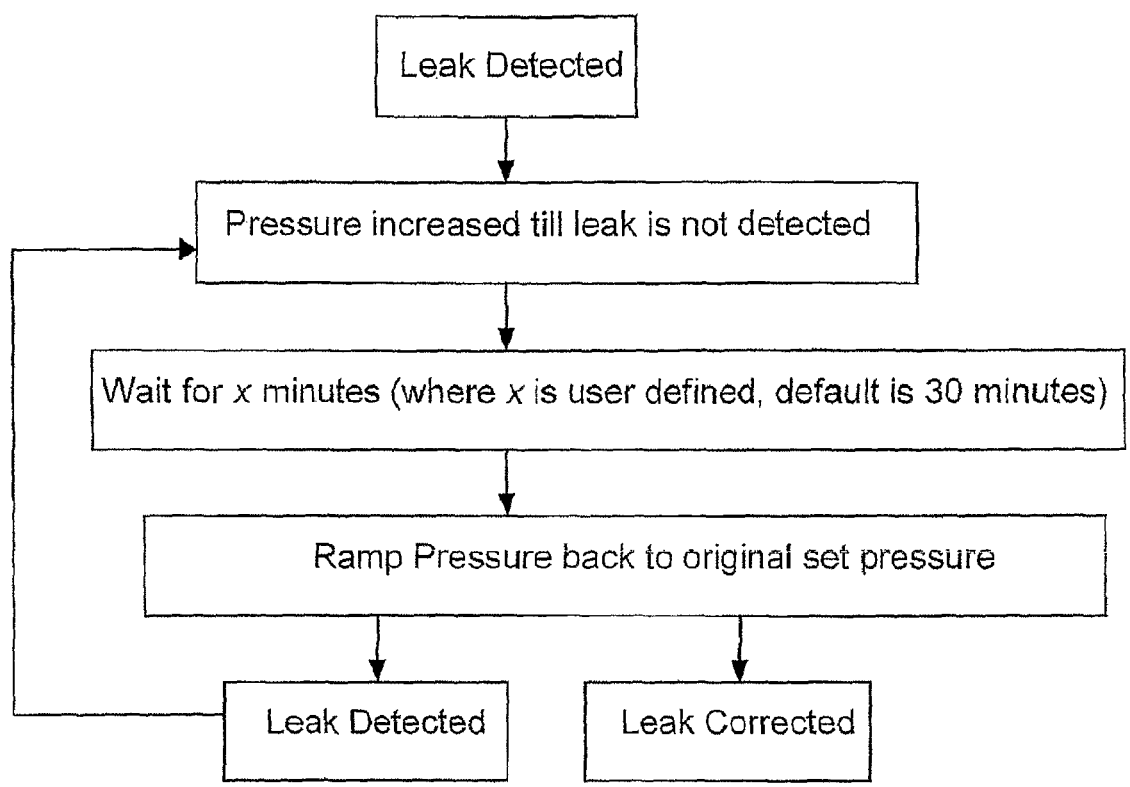
FIGS. 28-31 illustrate alternative methods for leak correction.

FIG. 28 illustrates a method for correcting leak in a single bladder cushion. As illustrated, the method includes detecting leak, increasing pressure until leak is not detected, waiting for a predetermined period of time, and ramping pressure back to the original set pressure. If leak is detected again, the method is repeated until leak is corrected.

9.1.2 Partitioned Single Bladder Cushion

Figure 29:
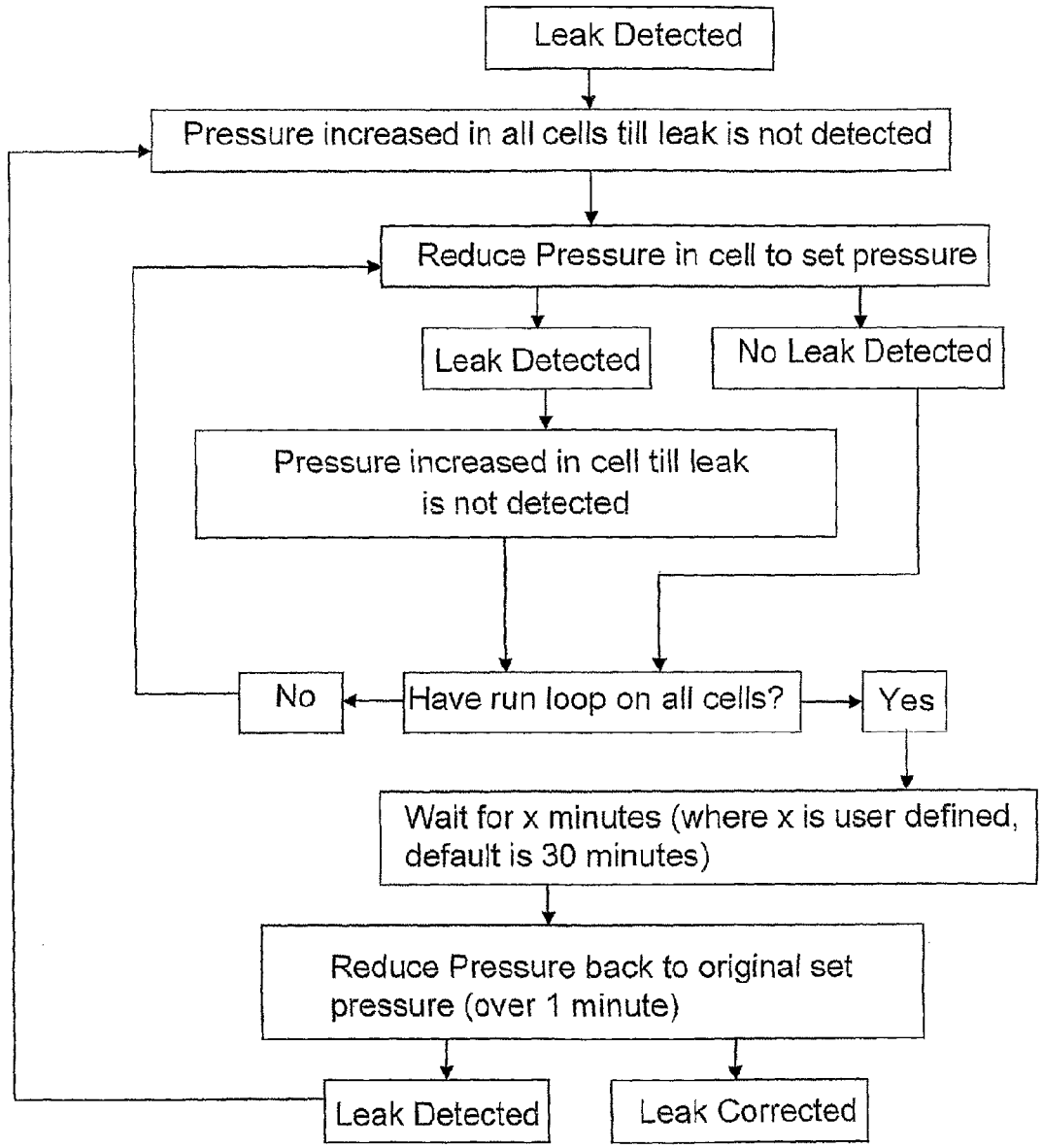

FIG. 29 illustrates a method for correcting leak in a partitioned single bladder cushion. As illustrated, the pressure of a cell is modified one at a time until leak is corrected.

For example, the method includes detecting leak, increasing pressure in all cells until leak is not detected, and reducing pressure in each cell one at a time to its set pressure. If leak is detected again, pressure is increased in each cell one at a time until leak is not detected.

Once no leak is detected, it is determined if a loop has been run on all cells. If no loop has been run on all cells, then the method returns to reducing/increasing pressure in each cell one at a time until leak is not detected. If a loop has been run on all cells, then the method includes waiting for a predetermined period of time and reducing pressure back to the original set pressure. If leak is detected again, the entire method is repeated until leak is corrected.

9.1.3 Concentric Bladder Cushion

Figure 30:
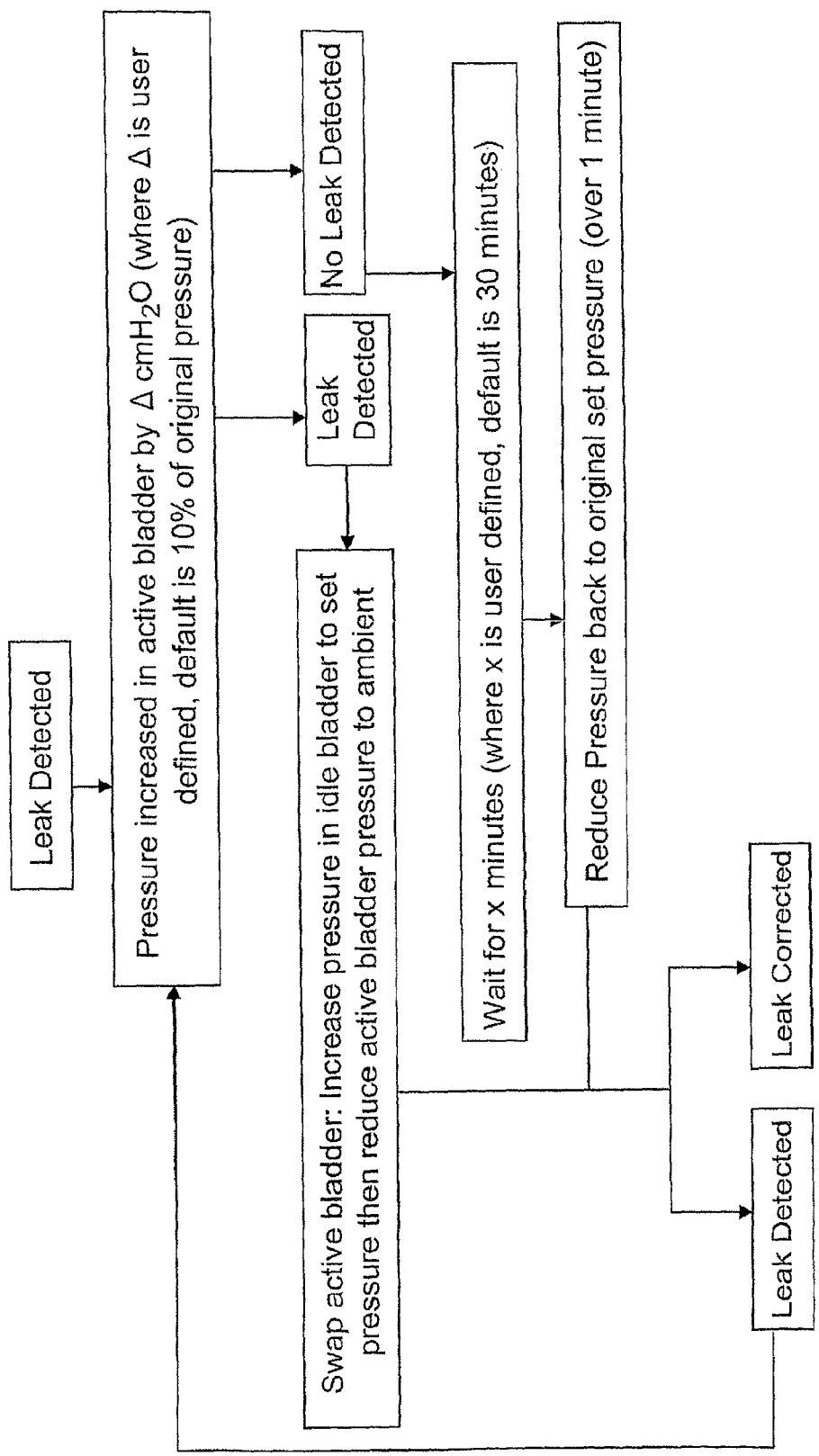

FIG. 30 illustrates a method for correcting leak in a concentric bladder cushion, i.e., cushion with multiple bladders. As illustrated, the active bladder may be swapped to correct the leak.

For example, the method includes detecting leak and increasing pressure in the active bladder by a predetermined amount. If leak is detected, the active bladder is swapped. The pressure is increased in the new active bladder to the set pressure, and the pressure is reduced in the previous active bladder to ambient pressure. If leak is still detected, then the method returns to increasing pressure in the active bladder by a predetermined amount. When no leak is detected following the pressure increase in the active bladder, the method includes waiting for a predetermined period of time and reducing pressure back to the original set pressure. If leak is detected again, the entire method is repeated until leak is corrected.

9.1.4 Partitioned Multiple Bladder Cushion

Figure 31:
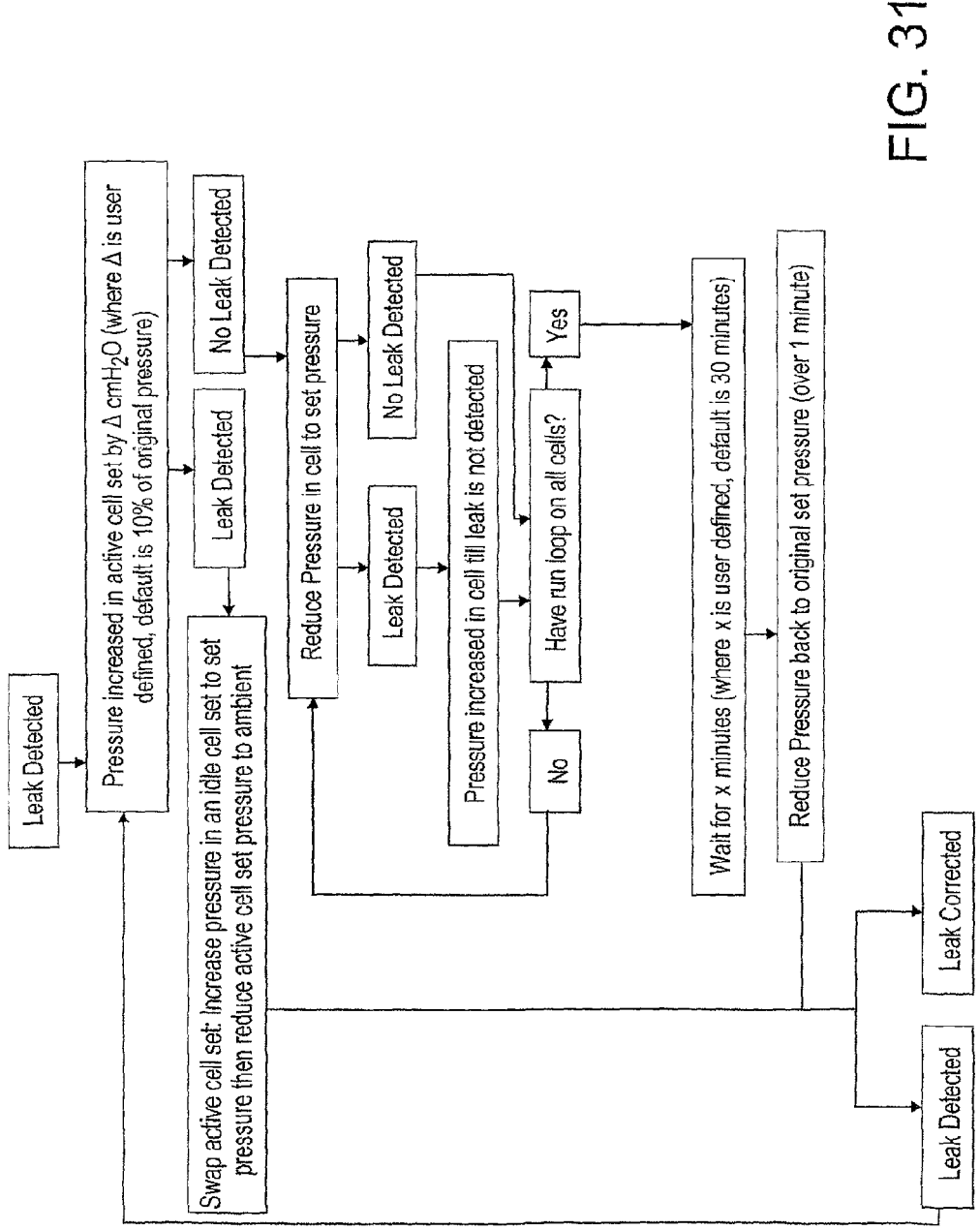

FIG. 31 illustrates a method for correcting leak in a partitioned multiple bladder cushion. As illustrated, the active cells may be swapped and/or the pressure of a cell is modified one at a time until leak is corrected.

For example, the method includes detecting leak and increasing pressure in the active cell set by a predetermined amount. If leak is detected, the active cell set is swapped. The pressure is increased in the new active cell set to the set pressure, and the pressure is reduced in the previous active cell set to ambient pressure. If leak is still detected, then the method returns to increasing pressure in the active cell set by a predetermined amount.

When no leak is detected following the pressure increase in the active cell set, the method includes reducing pressure in each cell one at a time to its set pressure. If leak is detected again, pressure is increased in each cell one at a time until leak is not detected.

Once no leak is detected, it is determined if a loop has been run on all cells. If no loop has been run on all cells, then the method returns to reducing/increasing pressure in each cell one at a time until leak is not detected. If a loop has been run on all cells, then the method includes waiting for a predetermined period of time and reducing pressure back to the original set pressure. If leak is detected again, the entire method is repeated until leak is corrected.

10. Variable Wall Thickness Bladder

Figure 32:
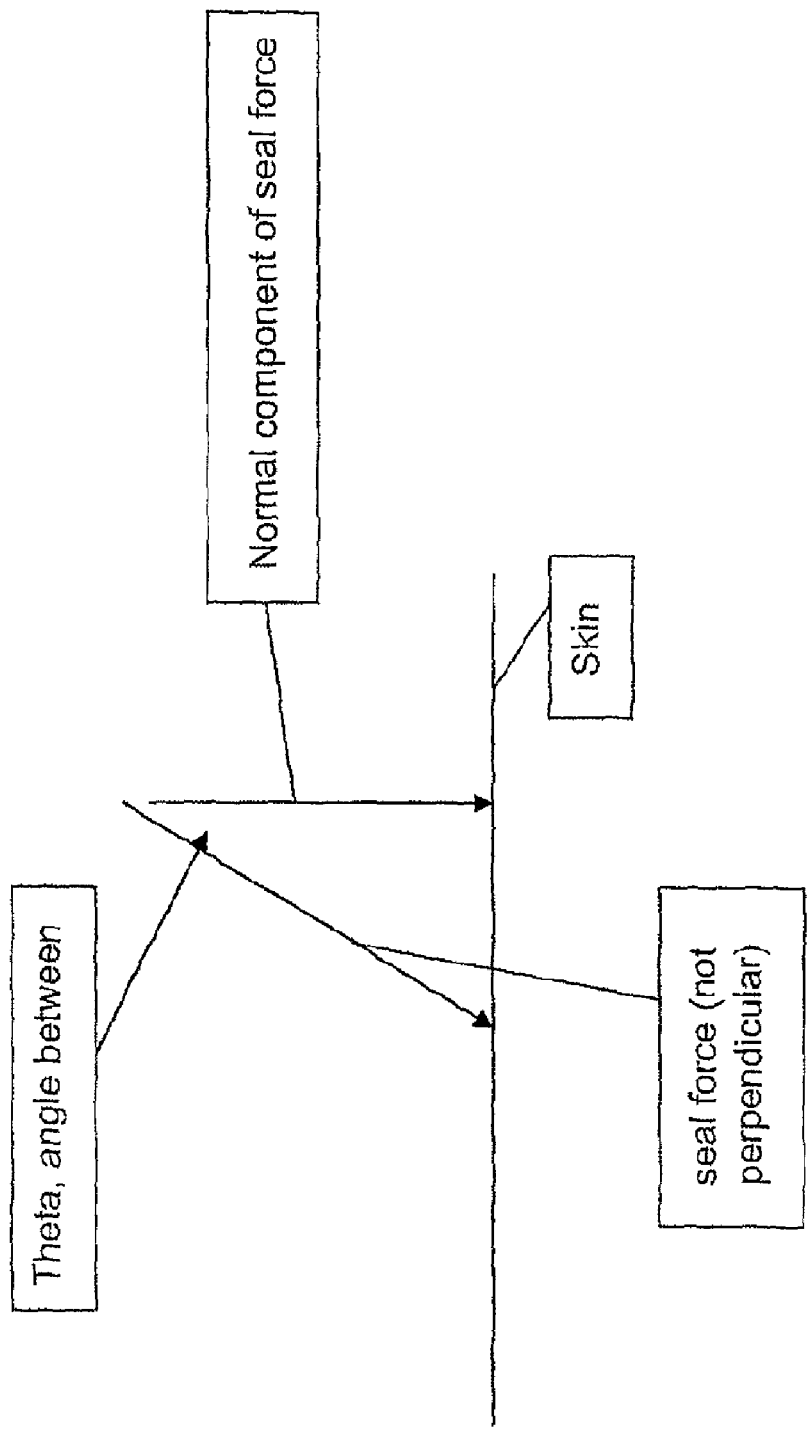
FIG. 32 is a schematic force diagram of sealing force.

The wall thickness of the bladder may be variable. This arrangement may help to control the direction of the pressure vector applied to the patient's face. For example, a thicker wall on the outer surface of the bladder and a thinner wall on the inside surface (i.e., skin side) of the bladder will create a force perpendicular or normal to the patient's skin. This is due to the higher flexibility of the thinner wall versus the thicker wall. A perpendicular seal force will be more efficient for sealing. That is, a perpendicular seal force will be higher than the same bladder pressure applied at a tangent and will be less likely to cause pressure sores. To seal the cushion against the patient's face, a certain magnitude of force normal to the patient's skin is required. As shown in FIG. 32, if the force being applied is not normal, a larger magnitude force will be required as (Force normal to the patient's skin=force×sin (theta)).

11. Manifold for Inflatable Bladder Cushion

To inflate the one or more bladders of a bladder cushion with an external pressure source, an access hole is required. In order to maintain seal force, the pressure within the bladder will be variable, and in proportion to the mask pressure. For VPAP treatment, this will represent a significant range of pressures for the bladder. For the cushion to seal correctly, the ratio of cushion pressure versus mask pressure shall be coordinated. If only one access hole is available, the pressure drop across this hole (resistance) will introduce a lag to the circuit. To prevent this, several access holes may be introduced to the cushion. These holes may be connected via a manifold to the external pressure source. The number of holes will be in proportion to the pressure drop across each hole from the manifold. The sum of the pressure drops over the holes (including path to manifold) shall be less than the pressure drop from the manifold to the external pressure source.

The manifold may be part of the frame, with channels within the frame to provide pressure to each of the access holes. Alternatively, the manifold may be external and attached to the end of the tube from an external pressure source, thereby providing pressure to the cushion via several small tubes.

12. Foam Insert

Figure 33:
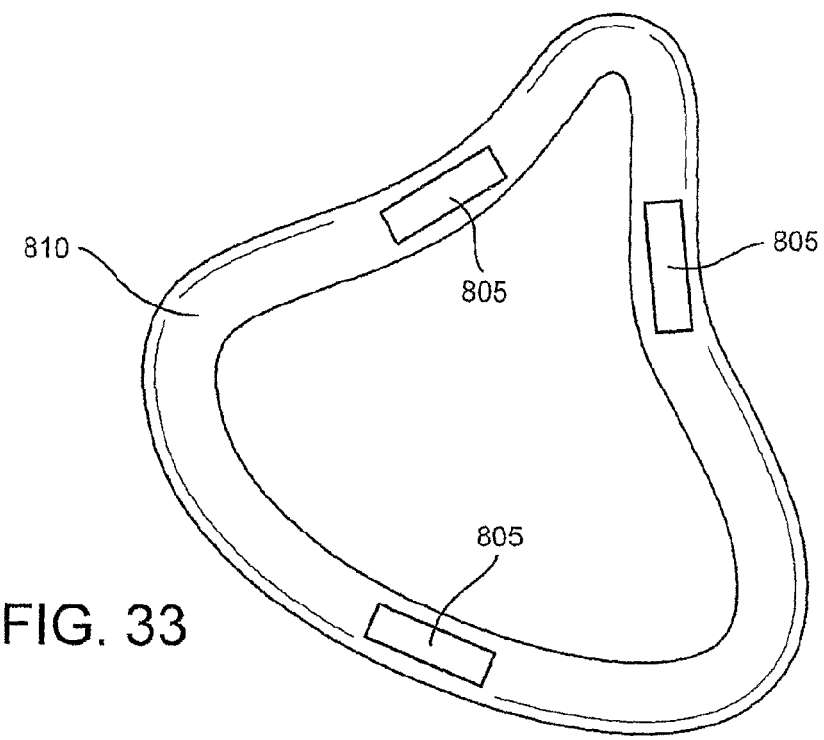
FIG. 33 is a schematic view of a cushion with foam inserts according to an embodiment of the present invention.

In an alternative embodiment, the contact pressure and/or contact points may be changed by using foam inserts to support the cushion. For example, different foam inserts may be used in the cushion from night to night, or foam inserts may be used in the cushion on alternate nights. FIG. 33 is a schematic view of a cushion 810 including foam inserts 805 to support the cushion 810. As illustrated, foam inserts 805 may be provided at different locations along the cushion perimeter to change the contact pressure and/or contact points. Also, foam inserts having different spring constants may be used. The stiffness of the inserts and therefore the contact pressure can also be changed by changing the density of the foam (one way to do this is by mechanical compression). Various foam inserts are disclosed in U.S. patent Ser. No. 10/533,928, the entirety incorporated herein by reference.

Furthermore, foam inserts may be used in combination with expandable bladders. In any of the above embodiments, the foam may be closed or open cell. The foam may be of any suitable durometer and/or density. Examples of suitable foams include silicone, polyurethane, latex, and polyolefin foams.

13. Force Location

Figure 34:
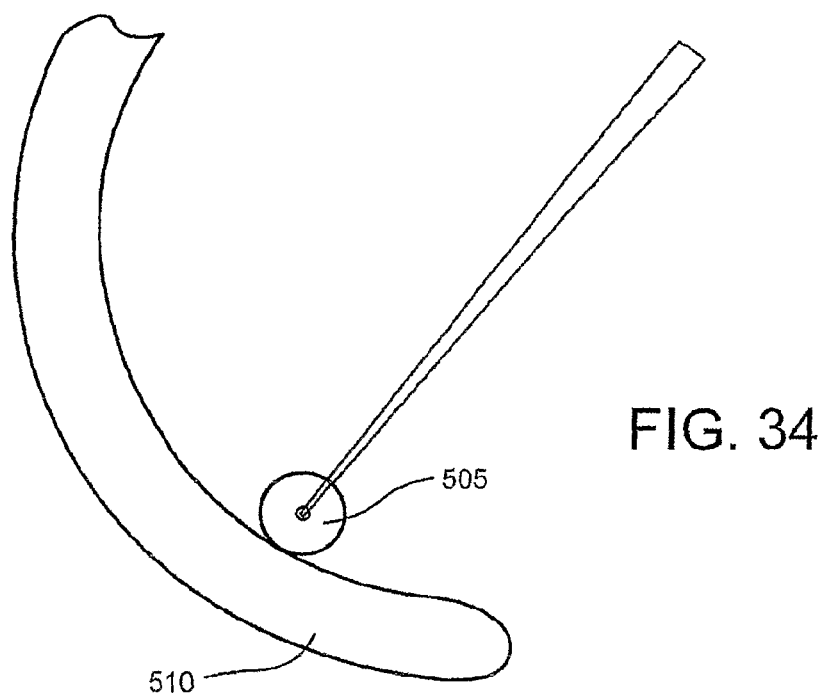
FIG. 34 is a schematic view of a rolling seal according to an embodiment of the present invention.

As noted above, changing the force location can improve patient comfort. For example, the force location may be alternated between two seal/cushion profiles or the two seal/cushion profiles may be utilized at the same time, e.g., see FIGS. 1 and 3. In an alternative embodiment, a rolling seal may be provided to change the force location. As shown in FIG. 34, the rolling seal may include a rolling wheel 505 that is movable along the sealing membrane 510 of a cushion to change the location of the force. However, the rolling seal may be provided by other functional equivalents, e.g., see FIG. 3 embodiment.

In another embodiment, a valve and a separate bladder may be provided within the internal volume of the mask. In use, the valve provides passage of fluid, e.g., air, from within the internal volume to the separate bladder. The bladder is configured to allow the sealing membrane of the mask cushion to move over the patient's skin to another position. The valve may be configured as a one-way valve that slowly pressurizes the bladder when the internal volume of the mask is pressurized by a patient's exhalation.

In yet another embodiment, the bladder may be inflated at the beginning of the night or treatment session. During the treatment session, the patients breathing slowly actuates a valve to the separate bladder to allow the bladder to deflate and the sealing membrane to roll along the patient's face. That is, the patient's breathing could either pump up the separate bladder or open a valve to release pressure from the separate bladder.

14. Force Magnitude

Changing the force magnitude can also improve patient comfort, e.g., massage mode described above. In an alternative embodiment, cushion materials may be incorporated into the cushion. The resilience of the cushion material may be adapted to change with the absorption of moisture or the cushion material may be adapted to change density with current. In either case, the change will cause the cushion membrane to roll and thereby move across the patient's face to provide skin relief.

15. Contact Force Area/Contact Force Vector

A variety of different headgear straps and/or headgear attachment points may be provided to a patient interface, e.g., mask. The different headgear arrangements allow the patient interface to be held and sealed to the patient's face in slightly different positions to allow respite for the normal sealing areas of the patient's face.

In an alternative embodiment, a gravity actuated mechanism may be incorporated into the patient interface. In use, when the patient rolls over during a treatment session, the mechanism is actuated, e.g., by a ball valve or mercury switch, to move the patient interface to a different position on the patient's face.

16. Tissue Oscillation

Figure 35:
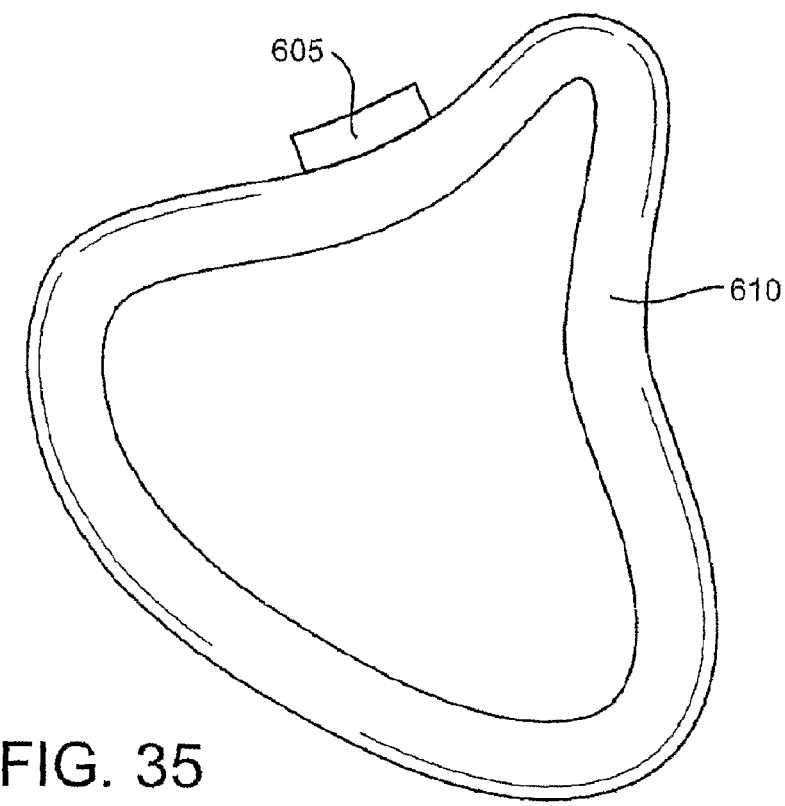
FIG. 35 is a schematic view of a cushion provided with a vibration mechanism according to an embodiment of the present invention.

In an alternative embodiment, as schematically shown in FIG. 35, a small, soft, and quiet vibration mechanism 605 may be provided to the cushion 610 to cause the cushion 610 to massage a patient's face, e.g., while he/she sleeps. This mechanism 605 may be configured to automatically turn on when the system detects that the patient is sleeping.

In another embodiment, the pressurized fluid, e.g., pressurized air, provided by the blower may be provided with a pulsing effect to massage a patient's face.

In another embodiment, a path for a viscous fluid or imbedded wires may be incorporated in the cushion to transfer vibrations to the patient's skin. In such an embodiment, the silicone material of the cushion may act as a dampener.

In another embodiment, bladders may contain a fluid with a high thermal coefficient of expansion. Thus, at least some bladders could be heated via a heating wire to change contact pressures.

In yet another embodiment, a vibration mechanism may be incorporated into the headgear to massage the patient's head (e.g., during or between treatment sessions).

In still another embodiment, a movable gusset may be incorporated into the cushion such that when the patient inhales/exhales the cushion can roll over the face.

17. Temperature

Figure 36:
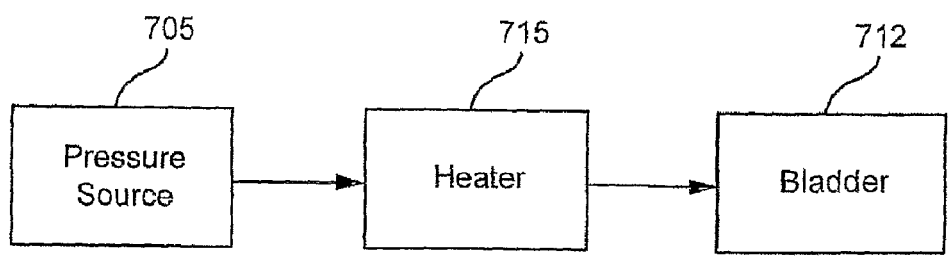
FIG. 36 is a schematic view illustrating heated fluid provided to a bladder according to an embodiment of the present invention.

It is known that heat aids in blood circulation and general comfort (especially in cooler climates/conditions). In an alternative embodiment, the fluid provided to the bladders described above may be heated before it is communicated to the bladder. For example, as schematically shown in FIG. 36, the pressurized fluid delivered by pressure source 705 may pass through a heater 715 before it is communicated to the bladder 712.

In another embodiment, biochemical snap heat packs or phase change material packs may be incorporated into the cushion. A phase change material is one that has a high heat of fusion, which, melting and solidifying at certain temperatures, is capable of storing or releasing large amounts of energy. Heating materials may also be provided in pockets in the cushion.

In yet another embodiment, additives may be introduced into the silicone material of the cushion (or the material the cushion is constructed of) so that the cushion may be heated in a microwave, for example.

If cooling the patient's skin would provide greater patient comfort, an evaporation mechanism may be incorporated into the cushion that wicks the patient's sweat and/or moisture in the air to provide evaporation cooling. Wicking the moisture away from the patient's skin is an associated benefit.

In another embodiment, an element or bladder may be provided to the cushion that is constructed from and/or includes a material with a melting temperature that corresponds to the temperature of the human body. This arrangement allows the patient's skin temperature to be used to modify the shape of the element or bladder and thereby modify the shape of the cushion. In an embodiment, the material may be a type of wax.

In yet another embodiment, an element or bladder may be provided to the cushion that is constructed from and/or includes a material that melts when pressure is applied to it (e.g., the melting point of the material substantially corresponds to the temperature of its surrounding). When the patient rolls at least partially onto the cushion, the element or bladder melts and collapses, thereby allowing some pressure relief.

18. Mask Pressure

In an embodiment, the frame that supports the cushion may be constructed relatively large so that pressure is more evenly spread over the patient's face.

19. Moisture Removal

Allowing moisture removal is another way to improve patient comfort. In an embodiment, moisture removal may be achieved by temporarily utilizing negative or high positive pressures to provide leaks. Leaks will allow the evaporation of moisture.

In another embodiment, the surface of the cushion may include dimples to allow a little air to leak out and thereby evaporate skin moisture.

In yet another embodiment, a cushion material may be selected that is normally corrugated but stretches flat under a small tensile load. When the patient inhales/exhales, a leak is produced to evaporate moisture.

In yet another embodiment, foam cells may be used that change porosity when stretched.

In yet another embodiment, the frame of the patient interface may be constructed to absorb and thereby store moisture until the moisture can be disposed of. Any suitable material that can absorb moisture may be used (e.g., a woven textile, a foam sponge, or other hydrophilic material).

In an alternative embodiment, sweat may be replaced with another liquid capable of wound healing.

20. Independent Region Adjustment (Localized Adjustment)

In an alternative embodiment, a large number of very small bladders, e.g., air bladders, may be incorporated into the cushion so that different groups of the bladders could operate at different times to provide relief to corresponding parts of the patient's face.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask for delivering breathable gas to a patient for treatment of sleep disordered breathing, the mask comprising:
   a cushion configured to interface with the patient's face, the cushion including two or more bladders arranged in concentric relation,
   each of the bladders including a face-contacting portion configured to engage the patient's face and form a continuous seal therewith, and each of the bladders is configured to be pressurized independently from one another,
   wherein at least one of the bladders is an active bladder that is pressurized to at least a sealing pressure to form the continuous seal with the patient's face in use.

2. The mask according to claim 1, wherein the bladders alternate as the active bladder that is pressurized to at least the sealing pressure to form the continuous seal.

3. The mask according to claim 1, wherein each of the bladders provides a contact position and a contact pressure against the patient's face.

4. The mask according to claim 3, wherein the bladders are alternately pressurized to alternate at least one of the contact position and the contact pressure provided by the bladders.

5. The mask according to claim 1, wherein each of the bladders is adapted to form a continuous seal around the patient's nose and mouth.

6. The mask according to claim 1, wherein each of the bladders is adapted to be pressurized by a fluid.

7. The mask according to claim 6, wherein the fluid is air.

8. The mask according to claim 1, wherein at least one of the bladders includes one or more partition walls that divide the bladder into two or more cells, and each of the cells is adapted to be pressurized independently from one another,
   wherein each of the cells is pressurized to at least a sealing pressure to form a portion of the continuous seal with the patient's face in use.

9. The mask according to claim 8, wherein the sealing pressure of each cell varies in different regions of the patient's face.

10. The mask according to claim 8, wherein the cells are alternately pressurized to alternate a contact pressure provided by each of the cells.

11. The mask according to claim 8, wherein the cells are adapted to form a continuous seal around the patient's nose and mouth.

12. The mask according to claim 8, wherein each of the cells is adapted to be pressurized by a fluid.

13. The mask according to claim 12, wherein the fluid is air.

14. The mask according to claim 1, wherein each of the bladders includes one or more partition walls that divide each bladder into two or more cells, and each of the cells of each bladder is adapted to be pressurized independently from one another,
   wherein selected cells of selected bladders are pressurized to at least a sealing pressure so that the selected cells cooperate to form the continuous seal with the patient's face in use.

15. The mask according to claim 14, wherein the cells of the bladders alternate as the selected cells that are pressurized to at least the sealing pressure to form the continuous seal.

16. The mask according to claim 14, wherein each of the cells provides a contact position and a contact pressure against the patient's face.

17. The mask according to claim 16, wherein the cells are alternately pressurized to alternate at least one of the contact position and the contact pressure provided by the cells.

18. The mask according to claim 14, wherein the sealing pressure of each cell varies in different regions of the patient's face.

19. The mask according to claim 14, wherein the selected cells are alternately pressurized to alternate a contact pressure provided by each of the cells.

20. The mask according to claim 14, wherein the selected cells are adapted to form a continuous seal around the patient's nose and mouth.

21. The mask according to claim 14, wherein the cells of one bladder are aligned with the cells of an adjacent bladder.

22. The mask according to claim 14, wherein the cells of one bladder are offset from the cells of an adjacent bladder.

23. The mask according to claim 14, wherein each of the cells is adapted to be pressurized by a fluid.

24. The mask according to claim 23, wherein the fluid is air.

25. A cushion for a patient interface, the cushion comprising:
- a bladder including a face-contacting portion adapted to engage the patient's face,
- the bladder adapted to be pressurized so that pressure within the bladder is alternated at a predetermined frequency to alternate contact pressure provided by the bladder,
- wherein pressure within the bladder is at least a sealing pressure to form a continuous seal with the patient's face in use, and
- wherein the bladder is substantially V-shaped at a first end portion thereof corresponding to the patient's nasal bridge region.

26. The cushion according to claim 25, wherein the bladder is adapted to form a continuous seal around the patient's nose and mouth.

27. The cushion according to claim 25, wherein the bladder is adapted to be pressurized by a fluid.

28. The cushion according to claim 27, wherein the fluid is air.

29. A mask for delivering breathable gas to a patient for treatment of sleep disordered breathing, the mask comprising:
- a cushion configured to interface with the patient's face, the cushion including a bladder having a face-contacting portion adapted to engage the patient's face, the bladder adapted to be pressurized
- wherein the bladder includes one or more partition walls that divide the bladder into two or more cells, and each of the cells is adapted to be pressurized independently from one another.

30. The mask according to claim 29, wherein the face-contacting portion is a forehead-contacting portion adapted to engage the patient's forehead.

31. The mask according to claim 30, wherein each of the cells provides a contact position and a contact pressure against the patient's forehead.

32. The mask according to claim 31, wherein the cells are alternately pressurized to alternate at least one of the contact position and the contact pressure provided by the cells.

33. The mask according to claim 30, wherein the cells are arranged horizontally and/or vertically in use.

34. The mask according to claim 30, wherein each of the cells is adapted to be pressurized by a fluid.

35. The mask according to claim 34, wherein the fluid is air.

36. A respiratory system comprising:
- a blower with a controller;
- a mask communicated with the blower, the mask including a cushion according to claim 1 wherein the controller is configured to operate the bladder in a massage-like manner.

37. The respiratory system according to claim 36, wherein the controller alternates pressure within the bladder at a predetermined frequency.

38. The respiratory system according to claim 37, wherein the controller alternates pressure within the bladder at least every minute.

39. The mask of claim 1, wherein the two or more bladders include first and second bladders, and the first bladder is nested within the second bladder.

40. The mask of claim 29, wherein the face-contacting portion is configured to engage the patient's face and form a continuous seal therewith.

* * * * *

UNITED STATES PATENT AND TRADEMARK OFFICE
CERTIFICATE OF CORRECTION

PATENT NO.        : 8,371,293 B2                                                Page 1 of 1
APPLICATION NO.   : 12/086288
DATED             : February 12, 2013
INVENTOR(S)       : Henry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1216 days.

Signed and Sealed this
First Day of September, 2015

Michelle K. Lee
*Director of the United States Patent and Trademark Office*